(12) United States Patent
Kanda et al.

(10) Patent No.: US 11,185,844 B2
(45) Date of Patent: Nov. 30, 2021

(54) CARRIER FOR ADSORBING ORGANIC MATTER

(71) Applicant: TORAY INDUSTRIES, INC., Tokyo (JP)

(72) Inventors: Shungo Kanda, Otsu (JP); Kaoru Shimada, Otsu (JP); Shunsuke Komachi, Otsu (JP); Hiroshi Takahashi, Otsu (JP); Hirofumi Yamanaka, Mishima (JP); Masato Masuda, Mishima (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

(21) Appl. No.: 17/058,951

(22) PCT Filed: Jul. 5, 2019

(86) PCT No.: PCT/JP2019/026762
§ 371 (c)(1),
(2) Date: Nov. 25, 2020

(87) PCT Pub. No.: WO2020/026698
PCT Pub. Date: Feb. 6, 2020

(65) Prior Publication Data
US 2021/0213421 A1    Jul. 15, 2021

(30) Foreign Application Priority Data

Jul. 31, 2018  (JP) .............................. JP2018-143340

(51) Int. Cl.
*B01J 20/28*  (2006.01)
*B01J 20/26*  (2006.01)
(Continued)

(52) U.S. Cl.
CPC ....... *B01J 20/28023* (2013.01); *B01J 20/261* (2013.01); *B01J 20/28071* (2013.01);
(Continued)

(58) Field of Classification Search
CPC .......... A61K 9/70; B01D 15/22; B01D 15/04; B01J 20/28023; B01J 20/28073;
(Continued)

(56) References Cited

U.S. PATENT DOCUMENTS

| 5,407,581 A | 4/1995 | Onodera et al. |
| 2010/0176051 A1 | 7/2010 | Shimagaki |

(Continued)

FOREIGN PATENT DOCUMENTS

| EP | 0314449 A2 | 10/1988 |
| JP | 60-209525 A | 10/1985 |

(Continued)

OTHER PUBLICATIONS

International Search Report, issued in PCT/JP2019/026762, PCT/ISA/210, dated Sep. 17, 2019.
(Continued)

*Primary Examiner* — Anthony J Zimmer
*Assistant Examiner* — Syed T Iqbal
(74) *Attorney, Agent, or Firm* — Birch, Stewart, Kolasch & Birch, LLP

(57) ABSTRACT

An object of the present invention is to provide a carrier for adsorbing organic matter, which achieves both of adsorption ability for organic matter and suppression of pressure increase. The present invention provides a carrier for adsorbing organic matter, comprising a sea-island type solid composite fiber, wherein the pore volume is 0.05 to 0.5 $cm^3/g$ and the fiber diameter is 25 to 60 μm.

17 Claims, 2 Drawing Sheets

(51) Int. Cl.
    *D01F 8/06*     (2006.01)
    *A61M 1/36*     (2006.01)

(52) U.S. Cl.
    CPC .......... *B01J 20/28073* (2013.01); *D01F 8/06* (2013.01); *A61M 1/36* (2013.01)

(58) Field of Classification Search
    CPC ..... B01J 20/28071; B01J 20/261; D01F 8/06; A61M 1/36
    See application file for complete search history.

(56) References Cited

U.S. PATENT DOCUMENTS

| | | | |
|---|---|---|---|
| 2010/0270232 A1 | 10/2010 | Iwanaga et al. | |
| 2012/0315477 A1* | 12/2012 | Tashiro | A45D 34/04 428/367 |
| 2016/0138225 A1* | 5/2016 | Cabell | D21H 11/12 162/123 |
| 2018/0065105 A1* | 3/2018 | Song | B01J 20/28035 |

FOREIGN PATENT DOCUMENTS

| | | | |
|---|---|---|---|
| JP | 2-84545 | A | 3/1990 |
| JP | 6-7429 | A | 1/1994 |
| JP | 2000-262894 | A | 9/2000 |
| JP | 2003064564 | A * | 3/2003 |
| JP | 2007-222596 | A | 9/2007 |
| JP | 2008-80114 | A | 4/2008 |
| JP | 4453395 | B2 | 4/2010 |
| JP | 2013-111551 | A | 6/2013 |
| JP | 5293599 | B2 | 9/2013 |
| JP | 2017-75355 | A | 4/2017 |

OTHER PUBLICATIONS

Written Opinion of the International Searching Authority, issued in PCT/JP2019/026762, PCT/ISA/237, dated Sep. 17, 2019.
Extended European Search Report for European Application No. 19844208.9, dated May 11, 2021.

* cited by examiner

CARRIER FOR ADSORBING ORGANIC MATTER

TECHNICAL FIELD

The present invention relates to a carrier for adsorbing organic matter.

BACKGROUND ART

In recent years, various carriers for adsorbing organic matter and columns packed with the carriers have been developed for the purpose of selectively separating and adsorbing a part of constituents from a liquid containing organic matter, particularly a liquid containing blood components. Among them, fibers having a large surface area per unit weight (hereinafter, specific surface area) are useful as carriers for adsorbing organic matter, and thus, carriers for adsorbing organic matter containing various fibers have been developed.

Patent Document 1 discloses an extracorporeal circulation column packed with an adsorbent for a tumor immunosuppressive substance, which adsorbs latent TGF-β. It has been reported that the specific surface area of the adsorbent packed in the column is preferably not less than 0.1 $m^2/g$, more preferably not less than 1 $m^2/g$.

Patent Document 2 discloses a detoxifying adsorbent in which a functional group having a chlorine-binding nitrogen atom and a polymyxin molecule are bound to an insoluble vinyl polymer molded article. The above detoxifying adsorbent is considered to be suitable for adsorption of endotoxins, and the preferable specific surface area of the insoluble vinyl polymer molded article is reported to be not less than 0.01 and 100 $m^2/g$ or less, more preferably not less than 0.05 and 10 $m^2/g$ or less.

Patent Document 3 discloses a fibrous structure for a treatment of biological components, which is made of fibers having an average diameter of less than 50 μm, wherein a part of the fibers is crimped, and a coefficient of change in the amplitude of the crimps is not less than 0.1. It has been reported that the above fibrous structure can be suitably used for treating biological components.

Patent Document 4 discloses a fibrous adsorbent in which a cross-linked polymer mainly composed of a vinyl aromatic compound is bound to the surface of a polyolefin fiber by a chemical bond.

Patent Document 5 discloses a method in which a sea-island composite fiber containing a poly(vinyl aromatic) polymer having a cross-linked structure as a sea component and polyolefin as an island component is swollen, and a cross-linked structure is further added to stabilize the swelling. As the fiber, a fiber having a macronet structure and a surface area of at least 100 $m^2/g$ or more is disclosed, and the diameter of the embedded filament is disclosed in the range of about 1 to about 10 μm.

PRIOR ART DOCUMENTS

Patent Documents

Patent Document 1: JP 4453395 B2
Patent Document 2: JP S60-209525 A
Patent Document 3: JP 5293599 B2
Patent Document 4: JP 2000-262894 A
Patent Document 5: JP H2-84545 A

SUMMARY OF INVENTION

Problem to be Solved by the Invention

In order to improve the adsorption efficiency of the carrier for adsorbing organic matter, it is common to add a ligand to strengthen the interaction of adsorption or to improve the specific surface area of the carrier. For example, in order to improve the specific surface area of the carrier, fibers having a small fiber diameter have been conventionally used. However, in this case, it was found that the pressure in the column was increased during the passage of a liquid. Thus, it was discovered that, with the conventional carrier for adsorbing organic matter, it was not possible to achieve both the improved adsorption ability by the improvement of the specific surface area and the suppression of the increase in the pressure during the passage of the liquid.

As a premise to exhibit the adsorption ability of the carrier for adsorbing organic matter, it is necessary that the carrier for adsorbing organic matter allow a liquid containing organic matter to pass stably. When the pressure increases during the passage of the liquid, the amount of the passing liquid becomes unstable, and the adsorption amount of the substance to be adsorbed cannot be controlled. Thus, the adsorption ability inherent to the carrier for adsorbing organic matter cannot be exhibited. Further, it is considered that, when the pressure increases remarkably, the passage of the liquid itself cannot be continued. Particularly, when the adsorption of a liquid containing blood components is carried out, an increase in pressure causes shear stress on the liquid containing blood components. As a result, there arises a problem of damage to the blood components. Since the pressure increase mainly occurs at the stage of the liquid passage through the carrier for adsorbing organic matter, the carrier for adsorbing organic matter is strongly required to have a reduced risk of the pressure increase as well as the adsorption ability.

Patent Document 1 discloses a specific surface area required for exhibiting the ability of the adsorbent. However, the fiber diameter of the fibers used in Examples is estimated from the manufacturing method to be about 4 to 5 μm, which brings up a concern that a pressure increase may occur depending on the usage. The idea regarding the fiber structure and the fiber diameter as well as the pores for achieving both the improvement of the adsorption ability and the suppression of the pressure increase is neither disclosed nor suggested.

Patent Document 2 discloses the specific surface area required for exhibiting the ability of an insoluble vinyl polymer molded article. However, the technique disclosed in Patent Document 2 is the improvement of the adsorption ability by using a functional group having a basic nitrogen atom and a polymyxin molecule as a ligand, and the improvement of the adsorption ability by increasing the pore volume of the fibers is not described. Further, the idea regarding the fiber structure and the fiber diameter as well as the pores for achieving both the improvement of the adsorption ability and the suppression of the pressure increase is neither disclosed nor suggested.

Patent Document 3 discloses an idea of suppressing the pressure increase by crimping fibers. However, since the fiber structure containing crimped fibers has a reduced bulk density, the packing amount of the fiber structure that can be packed in the column of the same volume decreases. As a result, the adsorption ability as the column lowers, and it is necessary to increase the volume of the column in order to achieve a high adsorption ability. When blood components are passed through, in order to prevent a pressure increase due to the retention inside the column, the volume of the column is required to be as small as possible to shorten the retention time. Thus, it is believed that it is difficult to achieve both the suppression of pressure increase and a high adsorption ability with the fiber structure of Patent Document 3. Further, although it is described that the average diameter of the fibers needs to be less than 50 µm, only the fibers of 5 µm are disclosed in Examples. Further, the idea regarding the fiber structure and the fiber diameter as well as the pores for achieving both the improvement of the adsorption ability and the suppression of the pressure increase is neither disclosed nor suggested.

Patent Document 4 discloses a technique for improving the surface area by modifying the surface of a polyolefin fiber with a cross-linked polymer. However, the fibrous adsorbent used in Examples is a non-woven fabric having a fiber diameter of 20 µm, which brings up a concern that a pressure increase may occur depending on the usage. Further, the idea regarding the fiber structure and the fiber diameter as well as the pores for achieving both the improvement of the adsorption ability and the suppression of the pressure increase is neither disclosed nor suggested.

Patent Document 5 discloses a fiber having a high surface area which is obtained by swelling a sea-island composite fiber having a cross-linked structure and further adding a cross-linked structure to stabilize the swollen structure. However, this technique improves the specific surface area by forming a macronet structure on the fiber surface, and there is no description about the improvement of the adsorption ability by increasing the pore volume. The objects to be adsorbed in Patent Document 5 is a gas, a vapor, and the like. In Examples, the adsorption amount to the adsorbent of dimethyl methylphosphonate which was placed still on the bottom of the desiccator was only evaluated over time. There is no specific disclosure regarding the effect of suppressing the pressure increase under dynamic conditions, for example, when a liquid is passed through the fiber. The idea regarding the fiber structure and the fiber diameter as well as the pores for achieving both the improvement of the adsorption ability and the suppression of the pressure increase is neither disclosed nor suggested.

Therefore, the development of a carrier for adsorbing organic matter, which achieves both the adsorption ability and the suppression of pressure increase, is demanded.

An object of the present invention is to provide a carrier for adsorbing organic matter, which achieves both of the high adsorption ability for organic matter and suppression of pressure increase.

Means for Solving the Problems

As a result of intensive study to solve the problems described above, the present inventors have found that a carrier for adsorbing organic matter which has a pore volume and a fiber diameter each controlled in an appropriate range can adsorb organic matter with high efficiency and can suppress the pressure increase of a column when the carrier is packed in the column.

That is, the present invention provides the following [1] to [7]:

[1] A carrier for adsorbing organic matter, comprising a sea-island type solid composite fiber, which has a pore volume of 0.05 to 0.5 cm$^3$/g and a fiber diameter of 25 to 60 µm.

[2] The carrier for adsorbing organic matter, according to [1], comprising a ligand having an acidic functional group or a basic functional group on the surface of the above sea-island type solid composite fiber, wherein the content of the above acidic functional group or the above basic functional group is 0.5 to 5.0 mmol per 1 g dry weight of the above sea-island type solid composite fiber.

[3] The carrier for adsorbing organic matter, according to [1] or [2], wherein the sea component of the above sea-island type solid composite fiber is composed of a single thermoplastic resin, and the island component of the above sea-island type solid composite fiber is composed of polyolefin.

[4] The carrier for adsorbing organic matter, according to any one of [1] to [3], wherein the distance from the surface of the above sea-island type solid composite fiber to the outermost island component in a cross section perpendicular to the fiber axis direction of the above sea-island type solid composite fiber is not less than 1 µm and less than 30 µm, and the maximum island diameter of the above island component of the above sea-island type solid composite fiber is 0.1 to 2 µm.

[5] The carrier for adsorbing organic matter, according to any one of [1] to [4], which is for adsorbing and removing blood components.

[6] A column for adsorption, comprising the carrier for adsorbing organic matter, according to any one of [1] to [5].

[7] A column for adsorption, comprising the carrier for adsorbing organic matter, according to any one of [1] to [5], wherein the packing density of the above carrier for adsorbing organic matter is 0.15 to 0.40 g/cm$^3$.

Effect of the Invention

The carrier for adsorbing organic matter of the present invention can achieve both of high adsorption ability for organic matter and suppression of pressure increase. Thus, the carrier for adsorbing organic matter can be used as a carrier for treatment of biological components, particularly for treatment of blood components, in the medical field.

MODE FOR CARRYING OUT THE INVENTION

Figure 1:
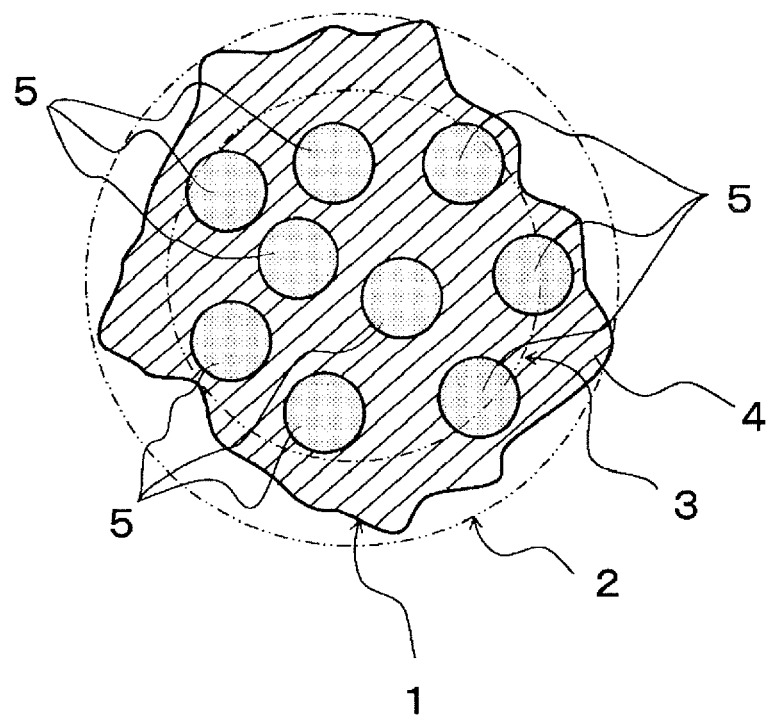
FIG. 1 is a view of a cross section perpendicular to the fiber axis of one example sea-island type solid composite fiber.

The present invention will now be described in detail.

The carrier for adsorbing organic matter of the present invention is characterized by comprising a sea-island type solid composite fiber which has a pore volume of 0.05 to 0.5 cm$^3$/g and a fiber diameter of 25 to 60 µm.

The "adsorption" means a state in which certain substances are adherent to a material and cannot be easily released from the material. The principle of adsorption is not particularly limited, but, for example, the adsorption means a state of adhesion by intermolecular force such as electrostatic interaction, hydrophobic interaction, hydrogen bonding, and Van der Waals force, and a state of physical adhesion such as cell adhesion, and phagocytosis of leukocytes.

The "organic matter" means a substance containing an organic compound, and its chemical structure and physical structure are not particularly limited. Examples thereof include biological components such as blood components, lymph components, viruses, and bacteria, in addition to fats and oils, pigments, and polymers. The organic matter as an object to be adsorbed by the carrier for adsorbing organic matter of the present embodiments is not particularly limited. Preferable examples as the objects to be adsorbed include biological components such as blood components, lymph components, viruses, and bacteria, which are, among organic matters, more likely to be damaged due to the pressure increase. Blood components are more preferable, and leukocyte components and cytokines are furthermore preferable especially in the case of purpose to treat inflammatory diseases.

The "carrier for adsorbing organic matter" means a carrier which has an ability of adsorbing organic matter, and the presence or absence of the ability of adsorbing other substances is not particularly limited as long as the ability of adsorbing organic matter is present. The carrier for adsorbing organic matter according to the present embodiments is preferably for adsorbing and removing blood components.

The carrier for adsorbing organic matter according to the present embodiments may be any one that contains a sea-island type solid composite fiber, and may be a sea-island type solid composite fiber alone or may be a sea-island type solid composite fiber immobilized or mixed with a suitable reinforcing material. The operation of the immobilizing or mixing may be carried out before or after the material is processed for the form.

The chemical structure of the reinforcing material is not particularly limited, and examples thereof include homopolymers containing as a monomer any one kind selected from the group consisting of ethylene glycol, butylene glycol, terephthalic acid, an aromatic vinyl compound (e.g., styrene, divinylbenzene), glucose, glucose triacetate, vinylpyrrolidone, vinyl alcohol, acrylonitrile, sodium methallylsulfonate, ethylene, propylene, ε-caprolactam and methyl methacrylate, copolymers containing as monomers two or more kinds selected from the above group, or mixtures obtaining by physically blending the above-described homopolymers, copolymers and the like. In view of not inhibiting the adsorption by the sea-island type solid composite fiber, the above-described reinforcing material is preferably a polymer having as a monomer a compound containing no aromatic ring and/or hydroxyl group. Specific examples thereof include homopolymers containing as a monomer any one kind selected from the group consisting of vinylpyrrolidone, acrylonitrile, sodium methallylsulfonate, ethylene, propylene, ε-caprolactam and methyl methacrylate, copolymers containing as monomers two or more kinds selected from the above group, or mixtures obtaining by physically blending the above-described homopolymers and copolymers. Among these, a polymer having ethylene and/or polypropylene (for example, polyethylene or polypropylene) as a monomer is preferable.

The "blood components" refer to components constituting blood, and examples thereof include humoral factors in blood and cells in blood. The blood components to be adsorbed by the carrier for adsorbing organic matter of the present embodiments are not particularly limited, but among blood components, humoral factors in blood are suitable as objects to be adsorbed.

The "humoral factors in blood" means organic matter dissolved in blood. Specific examples thereof include urea, proteins such as $\beta$2-microglobulin, cytokines, IgE and IgG, and polysaccharides such as lipopolysaccharides (LPS). Among these, urea, proteins such as cytokines, and polysaccharides such as LPS are generally preferable as objects to be adsorbed. Furthermore, cytokines are more preferable as objects to be adsorbed for the purpose to treat inflammatory diseases.

The "cytokines" means a group of proteins which, through a stimulus such as infection or trauma, are produced from various cells such as immunocompetent cells, released extracellularly, and allowed to act, and examples of cytokines include interferon-$\alpha$, interferon-$\beta$, interferon-$\gamma$, interleukin-1 to interleukin-15, tumor necrosis factor-$\alpha$, tumor necrosis factor-$\beta$, high-mobility group box-1, erythropoietin, or monocyte chemotactic factors.

The "cells in blood" means cells contained in blood, and examples of cells include leukocyte components such as granulocytes, monocytes, neutrophils, and eosinophils; erythrocytes; and platelets. Leukocyte components are preferable objects to be adsorbed for the purpose to treat inflammatory diseases. Among leukocytes, activated leukocyte or activated leukocyte-activated platelet complexes are more preferable, and activated leukocytes and activated leukocyte-activated platelet complexes are particularly preferable.

The "activated leukocytes" means leukocytes that are caused by cytokines, LPS, and the like to release cytokines, active oxygen, or the like, and examples of activated leukocytes include activated granulocytes and activated monocytes. The degree of activation can be determined by measuring the amount of activated oxygen released by activated leukocytes or measuring the expression of surface antigens by flow cytometry or the like. Examples of activated leukocytes include activated granulocytes and activated monocytes.

The "activated platelets" means platelets that are caused by cytokines, and the like to release cytokines, active oxygen, or the like.

The "activated leukocyte-activated platelet complexes" have no particular limitations on the types of the leukocytes as far as they are complexes wherein an activated leukocyte and an activated platelet are bound to each other to have a phagocytic activity into self-tissues and release cytokines, and examples thereof include activated granulocyte-activated platelet complexes and activated monocyte-activated platelet complexes. For treating patients with an inflammatory disease, in particular, it is considered to be necessary to remove activated granulocyte-activated platelet complexes that are considered to be directly related to the pathology.

The "inflammatory disease" collectively refers to a disease that initiates inflammatory reaction in the body. Examples of inflammatory diseases include systemic lupus erythematosus, malignant rheumatoid arthritis, multiple sclerosis, ulcerative colitis, crohn's disease, drug-induced hepatitis, alcoholic hepatitis, hepatitis A, hepatitis B, hepatitis C, hepatitis D, hepatitis E, sepses (for example, sepsis derived from gram-negative bacteria, sepsis derived from gram-positive bacteria, culture-negative sepsis, a fungal sepsis), influenza, acute respiratory distress syndrome (ARDS), acute lung injury (ALI), pancreatitis, idiopathic pulmonary fibrosis (IPF), inflammatory enteritis (for example, ulcerative colitis and crohn's disease), transfusion of a blood preparation, organ transplantation, reperfusion damage caused by organ transplantation, cholecystitis, cholangitis, or newborn blood group incompatibility, and the like. Among inflammatory diseases, preferable objects to be treated are drug-induced hepatitis, alcoholic hepatitis, hepatitis A, hepatitis B, hepatitis C, hepatitis D, hepatitis E, sepses (for example, sepsis derived from gram-negative bacteria, sepsis derived from gram-positive bacteria, culture-negative sepsis, and fungal sepsis), influenza, acute respiratory distress syndrome, acute lung injury, pancreatitis, and idiopathic interstitial pneumonia, which cause causative agents to be released in blood and can particularly be expected to be treated effectively with blood purification. For the application of the column for adsorption according to the present embodiments, preferable applications are the treatments for the foregoing inflammatory diseases, and among these, more preferable applications are the treatments for sepses (for example, sepsis derived from gram-negative bacteria, sepsis derived from gram-positive bacteria, culture-negative sepsis, and fungal sepsis), influenza, acute respiratory distress syndrome, acute lung injury, idiopathic pulmonary fibrosis, which are difficult to treat with pharmaceuticals alone and in which both cytokines and activated leukocyte-activated platelets are believed to be involved.

The sea-island type solid composite fiber has a cross-sectional structure in which island components composed of a certain polymer are scattered in a sea component composed of another polymer. The core-sheath type solid fiber is a sea-island type solid composite fiber having one island component. The cross-sectional shape of the sea-island type solid composite fiber is not particularly limited, but is preferably circular because it is less likely to be damaged by friction. The shape of the island component is not particularly limited. The processed form of the sea-island type solid composite fiber is not particularly limited. For example, yarn bundles, yarn, net, knitted fabric, and woven fabric which are processed from this fiber are preferable, and yarn bundles, knitted fabric, and woven fabric are more preferable, considering the large specific surface area and small flow path resistance.

The "sea-island type solid composite fiber" refers to a sea-island type composite fiber having no continuous void in the fiber axis direction of the fiber inside the sea-island type composite fiber, in other words, a sea-island type composite fiber having no hollow portion. When continuous voids or holes without continuity, having a diameter of less than 1 µm, are contained inside the sea-island type composite fiber, the fiber is regarded as solid rather than as hollow.

The sea component refers to a polymer present on the surface side of the sea-island type solid composite fiber.

The island component refers to a polymer of a different type from the sea component, which is scattered in the sea component when viewed in the direction perpendicular to the fiber axis direction of the sea-island type solid composite fiber. The material of the island component is not particularly limited as long as it is a component different from the sea component.

The "fiber diameter" is the average value of the diameters in a cross section obtained when the cross section in the direction perpendicular to the fiber axis direction is randomly observed at 100 positions by SEM. The fiber diameter herein is applied not only to columnar fibers but also to, for example, elliptical, rectangular or polygonal fibers. In this case, the smallest circle that can enclose the entire cross section (FIG. 1) perpendicular to the fiber axis direction (hereinafter, minimum enclosing circle, 2 in FIG. 1) is created, and the diameter of the minimum enclosing circle is calculated and considered as the diameter. For example, taking a star-shaped fiber having five protrusions as an example, the smallest circle that can enclose all the five vertices is created, and the diameter of the minimum enclosing circle is calculated. The same operation is performed at 100 positions, and the average value is used as the fiber diameter.

When the fiber diameter of the sea-island type solid composite fiber is less than 25 µm, a pressure increase occurs during the passage of a liquid. When the fiber diameter of the sea-island type solid composite fiber is more than 60 µm, the pores present in the fiber cannot be fully utilized, and the adsorption ability is reduced. Thus, the sea-island type solid composite fiber is required to have a fiber diameter of 25 to 60 µm. The fiber diameter of the sea-island type solid composite fiber is preferably 30 to 55 µm, more preferably 30 to 50 µm, and further preferably 35 to 50 µm. Any preferable lower limit can be combined with any preferable upper limit.

The circularity of the cross-sectional shape of the sea-island type solid composite fiber is not particularly limited, but too a large circularity results in the increase in the retention area of the liquid, which becomes the starting point of the pressure increase. Therefore, the circularity is preferably 0 to 15 µm.

The circularity herein refers to that defined in JISB0621-1984. Specifically, the circularity is, when a circular form is sandwiched by two concentric geometric circles, the difference in radius between the two concentric circles with the distance between the two circles being smallest.

A measurement method of the circularity will be described below.

In an image of a cross section of a sample cut perpendicular to the fiber axis direction, 10 positions are selected randomly and photographed at a magnification at which the island components can be clearly observed by SEM. A minimum enclosing circle (2 in FIG. 1) is created on the obtained images of the fiber cross sections, and the radius is calculated in units of 0.1 µm. Further, a maximum circle that is concentric with the minimum enclosing circle and can be included inside the fiber (hereinafter, maximum inscribed circle, 3 in FIG. 1) is created on the fiber cross sections, and the radius is calculated in units of 0.1 µm. The circularity is the value obtained by subtracting the radius of the maximum inscribed circle from the radius of the minimum enclosing circle.

The "pore volume" means the sum of volumes of minute pores which have a diameter of 200 nm or less and are contained in 1 g of the material. The pore volume is obtained by differential scanning calorimetry using a differential scanning calorimeter (hereinafter, DSC) in which the degree of freezing point depression due to capillary aggregation of water in the pores is measured. The pore volume is calculated as follows: the material to be measured is rapidly cooled to −55° C. and then heated to 5° C. with a temperature increment of 0.3° C./min to measure the differential scanning calorific value; and using the peak top temperature of the resulting curve as the melting point, the pore volume can be calculated by a theoretical formula. The above calculation method of the pore volume using the differential scanning calorimetry method and theoretical formula follows the method by Ishikiriyama et al., JOURNAL OF COLLOID AND INTERFACE SCIENCE, 1995, volume 171, pages 92-102 and pages 103-111). The "$V_{fp}$" in the above article corresponds to the pore volume in the present application. The pore volume is also referred to as the pore capacity, and is translated into "pore volume" in English.

Although the detailed mechanism is unknown, the adsorption ability cannot be sufficiently improved when the pore volume of the sea-island type solid composite fiber is too small. Therefore, the pore volume needs to be not less than 0.05 cm³/g. When the pore volume of the fiber is too large, the strength of the fiber is not maintained, fine particles are generated during the use, and the pores are not fully used, resulting in the lack of the adsorption ability. Therefore, the pore volume needs to be 0.5 cm³/g or less. That is, the pore volume of the sea-island type solid composite fiber needs to be 0.05 to 0.5 cm³/g. The pore volume is preferably 0.10 to 0.45 cm³/g, more preferably 0.15 to 0.40 cm³/g, and further preferably 0.15 to 0.34 cm³/g. Any preferable lower limit can be combined with any preferable upper limit. The preferable ranges of the above-described pore volume of the sea-island type solid composite fiber and the above-described fiber diameter of the sea-island type solid composite fiber can be optionally combined. In one embodiment, for example, the foregoing pore volume of the sea-island type solid composite fiber is of 0.10 to 0.45 cm³/g, and the foregoing fiber diameter of the sea-island type solid composite fiber is 30 to 55 μm. In another embodiment, the foregoing pore volume of the sea-island type solid composite fiber is of 0.15 to 0.40 cm³/g, and the foregoing fiber diameter of the sea-island type solid composite fiber is 30 to 50 μm. In another embodiment, the foregoing pore volume of the sea-island type solid composite fiber is of 0.15 to 0.34 cm³/g, and the foregoing fiber diameter of the sea-island type solid composite fiber is 30 to 50 μm. In another embodiment, the foregoing pore volume of the sea-island type solid composite fiber is of 0.15 to 0.34 cm³/g, and the foregoing fiber diameter of the sea-island type solid composite fiber is 35 to 50 μm.

The constituents of the sea-island type solid composite fiber are not particularly limited, but the sea component is preferably composed of a thermoplastic resin in view of processability. As the sea component, a single thermoplastic resin composed of one kind of thermoplastic resin, or a single thermoplastic resin composed of two or more kinds of thermoplastic resins completely compatible with each other may be used. Two or more kinds of thermoplastic resins which are incompatible with each other may be mixed or the like and used. Among these, the sea component is more preferably composed of a single thermoplastic resin in view of uniform adsorption of the substance. The island component is preferably composed of polyolefin in view of ensuring the strength. As the island component, a single polyolefin may be used, or two or more kinds of polyolefins may be mixed or the like and used. One preferable embodiment of the sea-island type solid composite fiber is, for example, a sea-island type solid composite fiber in which the sea component is composed of a single thermoplastic resin and the island component is composed of polyolefin. In another embodiment, the sea-island type solid composite fiber is a sea-island type solid composite fiber in which the sea component is composed of polystyrene and the island component is composed of polypropylene.

The "polyolefin" means a polymer synthesized by using olefins and alkenes as monomers, and among polyolefins, polypropylene or polyethylene is preferable as the island component of the sea-island type solid composite fiber in view of the strength.

The "thermoplastic resin" means a polymer material that can be plasticized and molded by heat, and is not particularly limited as long as it is a thermoplastic polymer material. Polymer materials containing a functional group which reacts with a carbon cation, such as an aryl group or a hydroxyl group, in a repeating structure, for example, polyethylene terephthalate, polybutylene terephthalate, poly(aromatic vinyl compound), polyester, polysulfone, polyether sulfone, polystyrene, polydivinylbenzene, cellulose, cellulose triacetate, polyvinyl pyrrolidone, polyacrylonitrile, sodium polymethallyl sulfonate, and polyvinyl alcohol can be preferably used. In particular, in the case of use for adsorbing blood components, as the above-described thermoplastic resin, one or more polymer materials selected from the group consisting of poly(aromatic vinyl compound), polyethylene terephthalate, polybutylene terephthalate, polystyrene, polysulfone, polyether sulfone, polydivinylbenzene, cellulose triacetate, polyvinylpyrrolidone, polyacrylonitrile and sodium polymethallyl sulfonate, which are polymer materials without hydroxyl groups, are preferably contained. Among them, polystyrene is particularly preferably contained because it has a large number of aromatic rings per unit weight, and various functional groups or reactive functional groups are introduced easily through Friedel-Crafts reaction or the like. These thermoplastic resins can be purchased commonly or can be produced by a known method.

The "single thermoplastic resin" has the same meaning as a homogeneous thermoplastic resin, and means one kind of thermoplastic resin or a thermoplastic resin constituted by two or more kinds of completely compatible thermoplastic resins. Among the single thermoplastic resins, polystyrene is preferable as the sea component of the sea-island type solid composite fiber. The composition of the sea component of the sea-island type solid composite fiber by a single thermoplastic resin can be confirmed by the absence of lumps of another thermoplastic resin which have a diameter of not less than 100 nm and are dispersed in the thermoplastic resin of the sea component by the TEM observation of the fiber cross section.

In view of improving the interaction with the organic matter to be adsorbed, the surface of the sea-island type solid composite fiber (in particular, the sea component on the surface) preferably contains (for example, by binding) a ligand having an acidic functional group or a basic functional group.

The "ligand" means a compound that binds to the surface of the sea-island type solid composite fiber, and the chemical structure thereof is not particularly limited as long as it has an acidic functional group or a basic functional group. Examples thereof include a compound having a sulfonic acid group or a carboxyl group which is an acidic functional group (anionic functional group) or a compound having an amino group which is a basic functional group (cationic functional group). In the present embodiments, the ligand is preferably a compound having a basic functional group, particularly a compound having an amino group. The above functional group may be used by combining a plurality of the same or different functional groups. The ligand may further include a neutral functional group as long as it includes the above acidic functional group or basic functional group. For example, the compound in which, as the neutral functional group, an alkyl group such as methyl or ethyl, or an aryl group such as phenyl group, a phenyl group substituted by alkyl (e.g., para(p)-methylphenyl, meta(m)-methylphenyl, ortho(o)-methylphenyl, para(p)-ethylphenyl, meta(m)-ethylphenyl, or ortho(o)-ethylphenyl), or a phenyl group substituted by a halogen atom (e.g., para(p)-fluorophenyl, meta(m)-fluorophenyl, ortho(o)-fluorophenyl, para(p)-chlorophenyl, meta(m)-chlorophenyl, or ortho(o)-chlorophenyl) is bound to the compound having the acidic functional group or basic functional group (e.g., tetraethylenepentamine to which para(p)-chlorophenyl is bound) is included in the ligand. In this case, the neutral functional group and the ligand may be bound directly, or may be bound via a spacer (a spacer involved in such a bonding is also referred to as a spacer 1). Examples of the spacer 1 include urea bonds, amide bonds, and urethane bonds.

The "acidic functional group or basic functional group" means a functional group having acidity or a functional group having basicity. Examples of the functional group having acidity include a sulfonic acid group, a carboxyl group, or the like. Examples of the functional group having basicity include an amino group, or the like. In the present embodiments, the basic functional group is preferable, and the amino group is more preferable. The above functional group may be used by combining a plurality of the same or different functional groups.

Examples of the "amino group" include amino groups derived from primary amines, such as methylamine, ethylamine, propylamine, butylamine, pentylamine, hexylamine, heptylamine, octylamine, or dodecylamine; amino groups derived from secondary amines, such as methylhexylamine, diphenylmethylamine, dimethylamine; amino groups derived from amines having unsaturated alkyl chain, such as allylamine; amino groups derived from tertiary amines, such as trimethylamine, triethylamine, dimethylethylamine, phenyldimethylamine, dimethylhexylamine; amino groups derived from amines having aromatic rings, such as 1-(3-aminopropyl)imidazole, pyridin-2-amine, 3-sulfoaniline; or amino groups derived from compounds in which two or more amino groups are bonded to alkyl chains, aromatic compounds, heterocyclic compounds, homocyclic compounds or the like (hereinafter, "polyamine"), such as tris(2-aminoethyl)amine, ethylenediamine, diethylenetriamine, triethylenetetramine, tetraethylenepentamine, dipropylenetriamine, polyethyleneimine, N-methyl-2,2'-diaminodiethylamine, N-acetyl-ethylenediamine, 1,2-bis(2-aminoethoxyethane). The amino group is preferably amino groups derived from polyamine, in particular, preferably amino groups derived from ethylenediamine, diethylenetriamine, triethylenetetramine, or tetraethylenepentamine, more preferably, amino groups derived from tetraethylenepentamine. In addition, the amino group is more preferably amino groups derived from primary amines or secondary amines.

The sea-island type solid composite fiber and the ligand having an acidic functional group or a basic functional group may be bound directly, or may be bounded through a spacer derived from a reactive functional group between the sea-island type solid composite fiber and the ligand (a spacer involved in such a bonding is also referred to as a spacer 2). The spacer 2 may be any ones that have an electrically-neutral chemical bond, such as urea bonds, amide bonds, ether bonds, ester bonds, or urethane bonds, and preferably one having amide bonds or urea bonds.

Examples of the reactive functional groups mediating the bonding between the sea-island type solid composite fiber and the ligand include activated halogen groups, such as haloalkyl groups (e.g., halomethyl groups or haloethyl groups), haloacyl groups (e.g., haloacetyl groups or halopropionyl groups) or haloacetamidealkyl groups (e.g., haloacetamidemethyl groups or haloacetamide ethyl groups); epoxide groups, carboxyl groups, isocyanic acid groups, thio-isocyanic acid groups, or acid anhydride groups. In the light of having a proper reactivity, the reactive functional group is preferably activated halogen group, more preferably haloacetamidealkyl group, and more particularly preferably haloacetamidemethyl group. Specific examples of the sea-island type solid composite fiber to which a reactive functional group is introduced include a sea-island type solid composite fiber having polystyrene as a sea component and polypropylene as an island component, with a chloroacetamidemethyl group introduced on the surface, and a sea-island type solid composite fiber having polysulfone as a sea component and polypropylene as an island component, with a chloroacetamidemethyl group introduced on the surface.

By reacting the sea-island type solid composite fiber with an appropriate reagent in advance, the reactive functional group can be introduced into the sea-island type solid composite fiber. For example, in cases where the sea component of the sea-island type solid composite fiber is polystyrene and the reactive functional group is a chloroacetamidemethyl group, the polystyrene and N-hydroxymethyl-2-chloroacetamide can be reacted to obtain a polystyrene to which chloroacetamidemethyl group is bound. To the polystyrene to which chloroacetamidemethyl group is bound, for example, tetraethylenepentamine having an amino group is reacted, thereby obtaining a polystyrene to which tetraethylenepentamine is bound through an acetamidemethyl group. In this case, the acetamidemethyl group corresponds to the spacer 2, and the tetraethylenepentamine corresponds to the ligand. Materials of the sea component of the sea-island type solid composite fiber, the spacers (spacer 1 and spacer 2), and the ligand can be optionally combined. Examples of the sea component to which the ligand is bound include a polystyrene to which a compound including amino groups derived from ethylenediamine, diethylenetriamine, triethylenetetramine, or tetraethylenepentamine is bound through an acetamidemethyl group; a polysulfone to which a compound including amino groups derived from ethylenediamine, diethylenetriamine, triethylenetetramine, or tetraethylenepentamine is bound through an acetamidemethyl group; and a polyethersulfone to which a compound including amino groups derived from ethylenediamine, diethylenetriamine, triethylenetetramine, or tetraethylenepentamine is bound through an acetamidemethyl group.

The content of the acidic functional group or the basic functional group is not particularly limited, but too small a content cannot sufficiently improve the adsorption ability for charged organic matter such as blood components, while too large a content improves the hydrophilic property and reduces the strength of the sea-island type solid composite fiber. Therefore, the content of the acidic functional group or the basic functional group is preferably 0.5 to 5.0 mmol per 1 g of dry weight of the sea-island type solid composite fiber, more preferably 0.5 to 2.0 mmol, further preferably 0.5 to 1.5 mmol, and still further preferably 1.0 to 1.5 mmol. Any preferable lower limit can be combined with any preferable upper limit.

The content of the acidic functional group or the basic functional group can be measured by an acid-base titration using hydrochloric acid or aqueous sodium hydroxide.

In the present description, in cases where the surface of the sea-island type solid composite fiber contains a ligand or the like, the ligand or the like is not included in the sea component. Only the sea component constituting the fiber structure of the sea-island type solid composite fiber is considered as the sea component of the sea-island type solid composite fiber.

The above ligand or the like herein means a chemical structure present on the surface of the sea component, and includes a structure derived from a ligand, spacer 1, spacer 2 and a reactive functional group, as well as a cross-linking agent.

On the surface of the sea-island type solid composite fiber, the position and orientation of the ligand-binding is not particularly limited. However, since the interaction with the substance to be adsorbed is necessary, in the sea component of the sea-island type solid composite fiber, the ligand is preferably bound to at least the surface side that comes into contact with organic matter such as blood. The surface herein means a surface of the sea-island type solid composite fiber, and when the surface has the form having pores, the most outer layer portion along the convexo-concave is included in the surface. Further, when the inside of the sea-island type solid composite fiber has through-holes, the surface includes not only the most outer layer portion of the sea-island type solid composite fiber but also outer layers of the through-holes inside the sea-island type solid composite fiber.

The structure of the fiber cross section perpendicular to the fiber axis direction of the sea-island type solid composite fiber is not particularly limited, but in view of suppressing the separation of the island component and the sea component, the distance from the surface of the sea-island type solid composite fiber to the outermost island component is not less than 1 µm and less than 30 µm, and the maximum island diameter of the island component of the sea-island type solid composite fiber is 0.1 to 2 µm.

The "distance from the surface of the sea-island type solid composite fiber to the outermost island component" means, in the cross section perpendicular to the fiber axis direction of the sea-island type solid composite fiber (also referred to as the longitudinal direction or the extension direction), the shortest distance from the surface of the sea-island type solid composite fiber to the island component on the outermost side in the fiber. When the island component is too close to the surface of the sea-island type solid composite fiber, the island component protrudes out of the fiber. On the other hand, when the island component is too far from the surface of the sea-island type solid composite fiber, the strength of the sea component cannot be maintained, causing a brittle fracture. Therefore, the distance from the surface of the sea-island type solid composite fiber to the outermost island component is preferably not less than 1 µm and less than 30 µm, more preferably not less than 1 µm and 10 µm or less, and further preferably not less than 1 µm and 5 µm or less.

The method for measuring the distance from the surface of the sea-island type solid composite fiber to the outermost island component is shown below.

Figure 2:
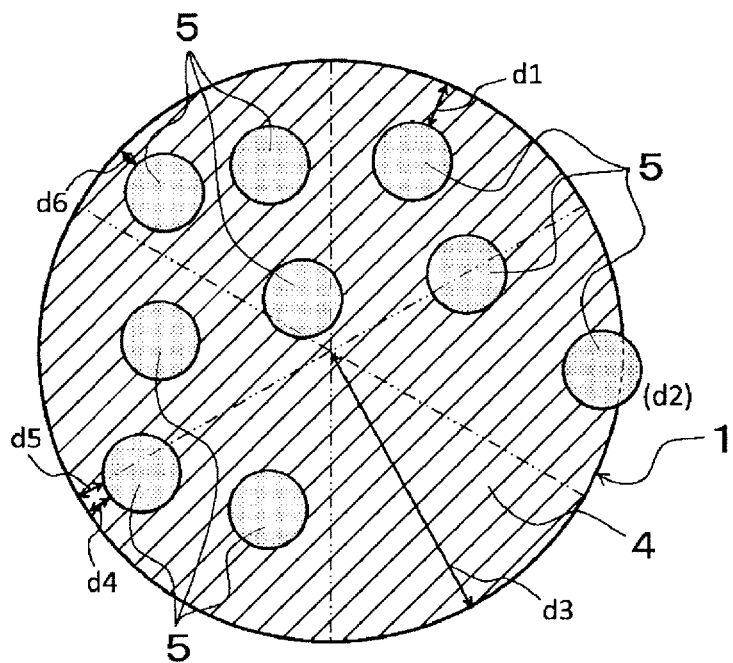
FIG. 2 is a view of a cross section perpendicular to the fiber axis of one example sea-island type solid composite fiber.

In an image of a cross section of a sample of the sea-island type solid composite fibers cut perpendicular to the fiber axis direction, 10 positions are selected randomly and photographed at a magnification at which the island components can be clearly observed by SEM. The obtained fiber cross-sectional image is divided into six parts by 60 degrees from the center of the fiber (chain double-dashed line in FIG. 2), and the shortest distance from the fiber surface to the outermost island component (d1 in FIG. 2) in each divided fiber cross section is measured in µm to one decimal place. When the fiber cross section has a deformed structure, the fiber is divided into six parts by 60 degrees from the center of the minimum enclosing circle and measured in the same manner. When an island component protrudes from the fiber surface, the distance is 0.0 µm (d2 in FIG. 2). When any island component is not present in the divided fiber cross section, the shortest distance from the center of gravity of the fiber cross section to the fiber surface (d3 in FIG. 2) is measured. When an island component spans a plurality of divided fiber cross sections and the island component is the outermost island component in the plurality of divided fiber cross sections, the shortest distance from the fiber surface in each of the divided fiber cross sections to the island component (d4, d5 in FIG. 2) is measured. The average value of the distances measured as described above in each of the divided fiber cross sections (for example, the average value of d1, d2, d3, d4, d5, and d6 in FIG. 2) is calculated for all the 10 images, and the average value thus obtained is defined as the distance from the surface of the sea-island type solid composite fiber to the outermost island component.

The "maximum island diameter" means the diameter of the largest island component which is observed in the cross section perpendicular to the fiber axis direction of the sea-island type solid composite fiber (also referred to as a longitudinal direction, extension direction). When the maximum island diameter of the island component of the sea-island type solid composite fiber is too large, the separation of the island component and the sea component is likely to occur, and when the maximum island diameter is too small, the strength of the island component is insufficient, and rupture is likely to occur. Therefore, the maximum island diameter is preferably 0.1 to 2 µm, more preferably 0.5 to 2 µm, and further preferably 0.5 µm to 1.5 µm. The preferable ranges of the above-described distance from the surface of the sea-island type solid composite fiber to the outermost island component and the above-described maximum island diameter of the island component of the sea-island type solid composite fiber can be optionally combined. In one embodiment, for example, the sea-island type solid composite fiber has a distance from the surface of the sea-island type solid composite fiber to the outermost island component of not less than 1 µm and less than 30 µm, and a maximum island diameter of the island component of the sea-island type solid composite fiber of 0.1 to 2 µm. In another embodiment, the sea-island type solid composite fiber has a distance from the surface of the sea-island type solid composite fiber to the outermost island component of not less than 1 µm and 10 µm or less, and a maximum island diameter of the island component of the sea-island type solid composite fiber of 0.5 to 2 µm. In still another embodiment, the sea-island type solid composite fiber has a distance from the surface of the sea-island type solid composite fiber to the outermost island component of not less than 1 µm and 5 µm or less, and a maximum island diameter of the island component of the sea-island type solid composite fiber of 0.5 to 1.5 µm. Each of the preferable ranges of the above-described pore volume of the sea-island type solid composite fiber, the above-described fiber diameter of the sea-island type solid composite fiber, the above-described distance from the surface of the sea-island type solid composite fiber to the outermost island component, and the above-described maximum island diameter of the island component of the sea-island type solid composite fiber can be optionally combined.

The method for measuring the maximum island diameter of the sea-island type solid composite fiber is shown below.

In an Image of a cross section of a sample of the sea-island type solid composite fibers cut perpendicular to the fiber axis direction, 10 positions are selected randomly and photographed at a magnification at which the island components can be clearly observed by a scanning electron microscope (SEM). In the 10 images thus obtained, the diameter of an island component randomly selected is measured at 100 positions, and the obtained diameters of the island components are compared. The diameter of the largest island component among them is defined as the maximum island diameter. The island diameter is not only applied to a columnar shape, but also applied to, for example, elliptical, rectangular, or polygonal ones. In this case, a minimum enclosing circle is created on one island component included in the cross section perpendicular to the fiber axis direction, and the diameter of the minimum enclosing circle is calculated and considered as the island diameter. For example, taking a star-shaped island component having five protrusions as an example, the smallest circle that can enclose all the five vertices is created, and the diameter of the minimum enclosing circle is defined as the island diameter.

The present invention also provides a column for adsorption, comprising the carrier for adsorbing organic matter as described above.

The "column for adsorption" means a column that has at least a liquid inlet portion, a case portion, and a liquid outlet portion, wherein the case portion is packed with the carrier for adsorbing organic matter. Examples of the column include a radial flow type column.

The column for adsorption of the present embodiments can adsorb organic matter from a liquid by passing the liquid to pass therethrough, and thus can be used in an application for purifying or removing target organic matter from the liquid containing organic matter. For example, it can be used for separation and the like of specific organic matter. Since the column for adsorption of the present embodiments is particularly suitable for adsorbing blood components, it is more preferably used as a column for adsorbing and removing blood components. The column for adsorbing and removing blood components herein is a column which has a function of removing waste products and harmful substances in blood components when a liquid containing blood components taken from a living body is passed through the column. The column for adsorption of the present embodiments is preferably used as a column for adsorbing and removing, in particular, proteins, toxins derived from microorganisms, leukocytes and the like among the blood components, and particularly preferably as a column for adsorbing and removing proteins. When the column for adsorption of the present embodiments is used for the treatment of inflammatory diseases, cytokines used for the transfer of the information of immune cells are preferable as objects to be adsorbed.

The container configuration of the column for adsorption may be any configurations as long as the container has an inlet and an outlet portions for a liquid containing organic matter (hereinafter referred to as a liquid) and a case portion in which the carrier for adsorbing organic matter can be packed. One embodiment is a container inside of which a cylindrical body formed by winding the carrier for adsorbing organic matter around a pipe into cylindrical form (hereinafter, cylinder) can be packed, and examples of the container include a container in which a liquid enters the cylinder from its circumference to flow into the inside of the cylinder, and then the liquid is discharged from the container; or a container in which a liquid enters the inside of the cylinder to flow into the outside of the cylinder, and then the liquid is discharged from the container. In view of production efficiency or inhibition of bypassing of the treated liquid, the container has preferably a structure in which the carrier for adsorbing organic matter is wound around a pipe whose side has pores. Specifically, examples thereof include a radial flow type container that includes a central pipe having pores on its longitudinal side, which pores are provided to flow a liquid out; the carrier for adsorbing organic matter which is packed around the central pipe and adsorbs the target substances contained in the liquid; a plate that is communicated with the upstream end of the central pipe such that the liquid passes through the inside of the central pipe, and that is arranged so as to prevent that the liquid does not pass the central pipe to come into contact with the carrier for adsorbing organic matter; a plate that blocks the downstream end of the central pipe, and that is arranged so as to immobilize the carrier for adsorbing organic matter to a space around the central pipe. Examples of the shape of the container include cylinder or prism such as triangular prism, quadrangular prism, hexagonal prism or octagonal prism, but are not limited to such structures. As another embodiment, there is a container that has a cylindrical space thereinside in which a carrier for adsorbing organic matter, that is cut out into circular shape, can be packed, and that has a liquid inlet and liquid outlet. Specifically, examples thereof include a container comprising thereinside a plate that comprises a liquid inlet provided to flow the supplied liquid out; a plate that comprises a liquid outlet provided to discharge the supplied liquid; and a cylindrical case portion in which the carrier for adsorbing organic matter, that is cut out into circular shape, is packed; which container has a liquid inlet and liquid outlet. In this case, the shape of the carrier for adsorbing organic matter is not limited to circular shape, and can be changed properly to any other shape of oval; polygon such as triangle or rectangle, trapezoid, or the like in accordance with the container configuration of the column for adsorption.

Examples of the container of the column for adsorption include those in glass, plastic or resin, stainless or the like. Size of the container is selected properly in accordance with intended use thereof and thus the size or the like of the container of the column for adsorption is not particularly limited. In view of operability in clinical sites or measurement locations or ease of disposal, the material is preferably made of plastics or resin and preferably has an easy-to-grip size. It is preferred that the height of the whole column for adsorption be not less than 1 cm and 30 cm or less, the external diameter be not less than 1 cm and 10 cm or less, and the internal volume be 200 $cm^3$ or less. In Examples described later, a column for adsorption having an internal volume of 11 $cm^3$ (packing height: 4.7 cm, packing diameter: 1.9 cm) and a column for adsorption having an internal volume of 145 $cm^3$ (packing height: 12.5 cm, packing diameter: 4.1 cm) were used for ease of measurement, but the present invention is not limited thereto.

The carrier for adsorbing organic matter is preferably packed by stacking one another in the column for adsorption. The stacking herein means to stack closely two or more of the carriers for adsorbing organic matter. Examples of methods for packing by stacking them include a method in which a plurality of the carriers for adsorbing organic matter, which are processed into sheet form, are stacked like an axial flow column; and a method in which the carrier for adsorbing organic matter, which is processed into sheet form, is wound around a pipe whose side has pores, like a radial flow column. Particularly packing by winding the carrier for adsorbing organic matter like a radial flow column is preferable.

The packing density of the carrier for adsorbing organic matter in the column for adsorption of the present embodiments is preferably 0.40 $g/cm^3$ or less because the pressure increase occurs frequently when the packing density is too high, while the packing density is preferably not less than 0.15 $g/cm^3$ because the ability cannot be sufficiently exhibited when the packing density is too low. That is, the packing density of the carrier for adsorbing organic matter in the column for adsorption is preferably 0.15 to 0.40 $g/cm^3$. In particular, the packing density is more preferably 0.20 to 0.40 $g/cm^3$, and further preferably 0.20 to 0.35 $g/cm^3$.

The combination of the packing method and the packing density of the carrier for adsorbing organic matter in the column for adsorption is not particularly limited, but for example, it is preferred that the carrier for adsorbing organic matter be stacked and packed in the column for adsorption, and that the packing density of the carrier for adsorbing organic matter be 0.15 to 0.40 $g/cm^3$. It is more preferred that the carrier for adsorbing organic matter be stacked and packed in the column for adsorption, and that the packing density of the carrier for adsorbing organic matter be 0.20 to 0.40 g/cm$^3$. As another combination, it is preferred that the carrier for adsorbing organic matter be wound around a pipe or the like which has pores and packed in the column for adsorption, and that the packing density of the carrier for adsorbing organic matter be 0.15 to 0.40 g/cm$^3$. It is more preferred that the carrier for adsorbing organic matter be wound around a pipe or the like which has pores and packed in the column for adsorption, and that the packing density of the carrier for adsorbing organic matter be 0.20 to 0.40 g/cm$^3$.

The "packing density" is a dry weight (g) of the carrier for adsorbing organic matter per internal volume (cm$^3$) before the carrier for adsorbing organic matter is packed in the case portion of the column. For example, in cases where the carrier for adsorbing organic matter having a dry weight of 1 g is packed in a container having an internal volume of 1 cm$^3$, the packing density is 1 g divided by 1 cm$^3$=1 g/cm$^3$.

The internal volume means a volume of a space packed with the carrier for adsorbing organic matter and can be calculated as a value obtained by subtracting the volume of a space where the carrier for adsorbing organic matter cannot be packed (hereinafter, dead volume) from the volume of the entire space through which the liquid passes in the column (hereinafter, packing volume). The dead volume is, for example, a space derived from a member for defining the flow path in the container, and includes the volume of the space inside the central pipe, the space of holes, the inlet portion and the outlet portion.

A measurement method of the above internal volume will be described below.

An empty column before being packed with the carrier for adsorbing organic matter is filled with water in a way that air does not enter. All the packed water is taken out to the graduated cylinder, and the amount of the water taken out is confirmed. Then, the packing volume is calculated from the obtained amount of packing liquid given that 1 mL of water is 1 cm$^3$. The dead volume is calculated by measuring with a ruler, calipers, or the like, each volume occupied by the member of a portion that cannot be packed with the carrier for adsorbing organic matter and adding them. From these values, the internal volume can be calculated by the following Equation 1.

Internal Volume (cm$^3$)=Packing Volume (cm$^3$)−Dead Volume (cm$^3$)   Equation 1

The method for measuring the dry weight of the carrier for adsorbing organic matter packed in the column for adsorption will be described below.

A carrier for adsorbing organic matter having the same volume as the internal volume of the column is prepared. When a carrier for adsorbing organic matter which has already been packed in the column is analyzed, the entire amount of the carrier for adsorbing organic matter in the column is taken out. The carrier for adsorbing organic matter is vacuum-dried in a vacuum dryer set to 30° C., the dry mass is measured by an electronic balance, and the obtained value (g) is defined as the dry mass. For the confirmation of the dryness, the difference in mass of 1% or less when the dry mass is measured twice can be used as an index. When the dry mass is measured twice, the interval is one hour.

The carrier for adsorbing organic matter of the present embodiments can be produced using a method, for example, but not limited to, the following method.

When a reinforcing material is immobilized or mixed with the sea-island type solid composite fiber, methods of immobilizing or mixing both are not particularly limited, but include physically mixing by a needle punch or the like, or heating to a glass transition temperature or higher, followed by molding.

The fiber diameter of the sea-island type solid composite fiber can be decreased by reducing the discharge amount of the polymer during spinning and increasing the winding speed. Further, when a ligand is introduced, the fiber diameter can be increased due to the swelling by impregnation with a solvent upon the introduction of the ligand. Therefore, the fiber diameter can be controlled within a target range by appropriately adjusting the conditions.

The distance from the surface of the sea-island type solid composite fiber to the outermost island component in the cross section perpendicular to the fiber axis direction of the sea-island type solid composite fiber can be controlled by arranging the distribution holes for the island component in the central portion of the spinneret and the distribution holes for the sea component in the peripheral portion of the spinneret, and then joining them for the discharge from the spinneret. Further, the distance can be thickened by increasing the discharge amount of the sea component polymer and decreasing the discharge amount of the island component polymer during spinning.

The maximum island diameter of the island component of the sea-island type solid composite fiber can be decreased by increasing the number of divisions for the island component in the distribution plate to make the distribution holes narrower in the spinneret, decreasing the area ratio per spinneret, increasing the discharge amount of the sea component polymer during spinning, or decreasing the discharge amount of the island component polymer during spinning.

The pore volume of the sea-island type solid composite fiber can be controlled by the production method of impregnating the sea-island type solid composite fiber with a solvent, followed by etching. For example, the pore volume can be increased by impregnating the sea-island type solid composite fiber with a solvent in which the sea component is easily dissolved. The pore volume can be also increased by adding a cross-linking agent and a catalyst to the mixture solution at the same time. Thus, the pore volume can be controlled within a target range by appropriately adjusting the conditions.

In cases where the sea component is polystyrene, examples of the foregoing solvent include nitrobenzene, nitropropane, chlorobenzene, toluene, and xylene, and preferably nitrobenzene and nitropropane.

Examples of the cross-linking agent include aldehyde compounds such as paraformaldehyde, acetaldehyde or benzaldehyde.

Examples of catalysts for cross-linking include Lewis acids such as sulfuric acid, hydrochloric acid, nitric acid, halogenated aluminium (III) (for example, aluminium chloride (III)), and halogenated iron (III) (for example, ferric chloride (III)). Sulfuric acid or ferric chloride (III) is preferably mixed.

The concentration of a catalyst in the mixture solution is preferably 5 to 80 wt %, more preferably 30 to 70 wt %.

The impregnation temperature is preferably 0 to 90° C., more preferably 5 to 40° C.

The impregnation time is preferably 1 minute to 120 hours, more preferably 5 minutes to 24 hours.

The method for modifying a sea-island type solid composite fiber with a ligand is described below. A sea-island type solid composite fiber is added to a solution of a Lewis acid (for example, aluminium (III) chloride) and carbamoyl chloride having a haloalkyl group (for example, N,N-bis(2-chloroethyl)carbamoyl chloride) dissolved in a non-polar solvent (for example, dichloromethane) and stirred to obtain a carbamoyl chloride-binding sea-island type solid composite fiber. Alternatively, a sea-island type solid composite fiber is added to a solution of protic acid (for example, sulfuric acid) and a chloroacetamide having a haloalkyl group (for example, N-hydroxymethyl-2-chloroacetamide) dissolved in a non-polar solvent (for example, nitrobenzene) and stirred to obtain a chloroacetamide-binding sea-island type solid composite fiber. Subsequently, as a ligand, to a solution, for example, of a compound having an amino group (hereinafter also referred to as an amine compound; for example, tetraethylenepentamine) dissolved in dimethyl sulfoxide (hereinafter, DMSO), the foregoing carbamoyl chloride-binding sea-island type solid composite fiber or the foregoing chloroacetamide-binding sea-island type solid composite fiber is added, and reacted. Thus, a sea-island type solid composite fiber having an amine compound as a ligand introduced on the surface can be obtained. Furthermore, by adding and reacting the sea-island type solid composite fiber having an amine compound introduced as a ligand on the surface to a solution in which a compound having reactivity with an amino group (for example, chlorophenylisocyanate) is dissolved, the amine compound introduced on the fiber surface can be further modified. The timing of modifying the amine compound is not particularly limited. The modification reaction may be, as described above, carried out on the sea-island type solid composite fiber in which the amine compound has been introduced on the surface, or the amine compound and the compound having reactivity with an amino group may be reacted in advance before reacting the carbamoyl chloride-binding sea-island type solid composite fiber or the chloroacetamide-binding sea-island type solid composite fiber with the amine compound. In the latter case, a compound having a modified amino group, which is obtained by reacting the amine compound with the compound having reactivity with an amino group, is used as a ligand, and can be introduced to the carbamoyl chloride-binding sea-island type solid composite fiber or a chloroacetamide-binding sea-island type solid composite fiber.

The timing of the ligand modification to the sea-island type solid composite fiber is not particularly limited, and the modification may be carried out before or after the shape of the sea-island type solid composite fiber is processed. A polymer to be a sea component (for example, polystyrene) is added to a solution of a Lewis acid (for example, aluminium (III) chloride) and a hydroxyalkyl compound having a haloalkyl group (for example, hydroxymethyl chloride) dissolved in a non-polar solvent (for example, dichloromethane) and stirred to obtain polychloromethylstyrene. Subsequently, as a ligand, to a solution, for example, of an amine compound (for example, tetraethylenepentamine) dissolved in DMSO, the foregoing polychloromethylstyrene is added and reacted. Thus, polystyrene having an amine compound as a ligand introduced on the surface can be obtained. Polystyrene having an amine compound introduced as a ligand on the surface and, for example, a different type of polymer (for example, polypropylene) are separately melted and metered in a spinning machine, and flowed into a spinning pack which integrates a sea-island composite spinneret in which distribution holes for the island component are formed. This sea-island composite flow is then melt-discharged. Thus, a sea-island type solid composite fiber in which an amine compound is introduced as a ligand on the surface can be obtained.

Examples of the method for evaluating the adsorption ability of the carrier for adsorbing organic matter include a method for measuring the adsorption rate of sodium p-(2-hydroxy-1-naphthylazo)benzenesulfonate (hereinafter referred to as acid orange 7). Acid orange 7 is a type of dye, and is known to be adsorbed to an adsorbent material by intermolecular force, and thus is suitable as organic matter for evaluating the adsorption ability. A higher adsorption rate of the acid orange 7 is judged to indicate a higher adsorption ability of the carrier for adsorbing organic matter.

In the above evaluation method, since the adsorption of the acid orange 7 is considered to be a reaction in equilibrium, it is considered that the adsorption equilibrium is reached when the adsorption treatment is carried out for about 5 hours, independently of the concentration of the acid orange 7.

For the above reason, the adsorption rate of the acid orange 7 preferably reaches 100% in 5 hours. Therefore, the adsorption rate of the acid orange 7 is preferably not less than 40% in 2 hours, and more preferably not less than 50%.

As another evaluation method, the adsorption rate of interleukin 8 (hereinafter, IL-8), the adsorption rate of interleukin 6 (IL-6), the adsorption rate of high mobility group box-1 (HMGB-1), or the like is measured. IL-8, IL-6 and HMGB-1 are a type of cytokines contained in blood components and are suitable blood components for evaluation of the adsorption ability. A higher adsorption rate of IL-8 IL-6, and HMGB-1 is judged to indicate a higher adsorption ability of the carrier for adsorbing organic matter, particularly a higher adsorption ability for blood components. In particular, the adsorption rate of IL-8 is one of the representative biomarkers in inflammatory diseases, and thus can be suitably used.

The presence or absence of the pressure increase during the use of the carrier for adsorbing organic matter can be evaluated by measuring the possible duration of liquid passage through the column. The possible duration of liquid passage through the column means, when the organic matter is blood components, the duration during which the difference between the inlet pressure and the outlet pressure is 100 mmHg or less when the column provided with the carrier for adsorbing organic matter and a blood vessel of an animal are connected, and blood is taken out at a constant rate and continuously passed through the column. Since there is a risk of damaging blood components when a pressure increase occurs in the extracorporeal circulation, the pressure increase is a phenomenon that should be avoided in view of safety. In addition, when the pressure increase occurs, the adsorption amount of blood components and the like becomes unstable, so there is a risk that the adsorption ability of the column cannot be sufficiently exhibited. If the above possible duration of liquid passage through the column is too short, the blood components and the like cannot be adsorbed sufficiently. Therefore, it is necessary that the liquid passage can be performed continuously for at least 60 minutes or more, and it is particularly preferable that the liquid passage can be performed for not less than 120 minutes.

In order to ensure the possible duration of liquid passage through the column, the pressure loss during the circulation of blood cell-free serum in the column packed with the carrier for adsorbing organic matter is preferably low. The pressure loss means the difference between the inlet pressure and the outlet pressure when the column provided with the carrier for adsorbing organic matter and pooled serum are connected, and the serum is continuously passed through the column at a constant rate. A high pressure loss is likely to cause clogging during blood circulation, and the risk of the pressure increase gets higher. Although the value of the pressure loss is not specified, it is preferably 100 mmHg or less, more preferably 30 mmHg or less.

Figure 3:
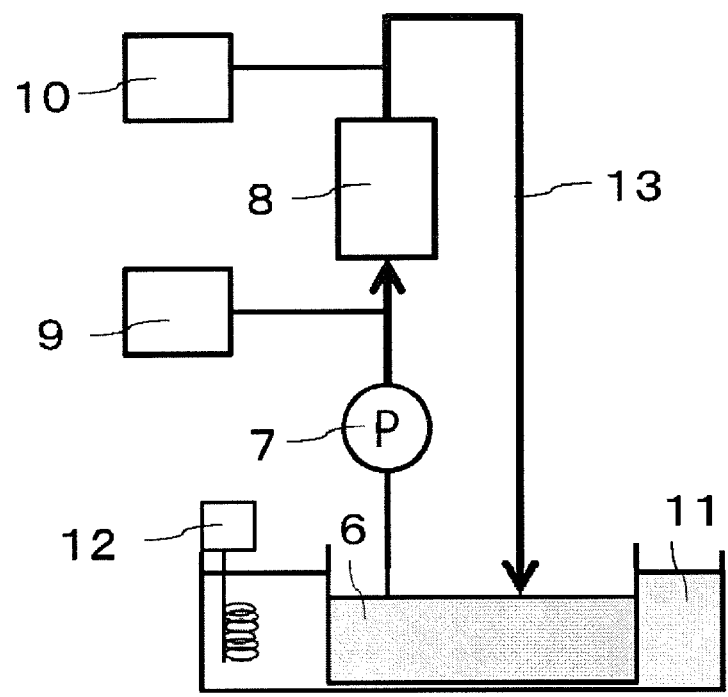
FIG. 3 is a schematic view of a circuit and a device used in a pressure loss measurement test.

The pressure loss can be measured by passing a fetal bovine scrum (hereinafter, FBS) solution through the column for adsorption packed with the carrier for adsorbing organic matter. A specific measurement method will be described below. A carrier for adsorbing organic matter is first packed in a container having a liquid inlet/outlet. The packing density of the carrier for adsorbing organic matter can be optionally adjusted by changing the packing method. Next, the FBS solution is allowed to pass through the container at a given flow rate, and the inlet pressure and outlet pressure are each measured. Then, a pressure loss can be determined by subtracting the outlet pressure value from the inlet pressure value. The flow rate (mL/min) of the FBS solution in measurement and the amount of the FBS solution used for a pool are set on the basis of 100 mL/min and 2500 mL per 145 $cm^3$ of container volume, taking clinical practice of blood purification into consideration. For example, if the container volume is 5 $cm^3$, the flow rate is 100 mL/min÷145 $cm^3$×5 $cm^3$=3.4 mL/min, and the amount of the FBS solution is set to 2500 mL÷145 $cm^3$×5 $cm^3$=29 mL for the measurement. A schematic view of a circuit and a device used in a pressure loss measurement test is shown in FIG. 3. In FIG. 3, the pooled FBS solution 6 is sucked up using a pump 7 and is allowed to pass through the column for adsorption 8. At this time, an inlet pressure measurement device 9 and an outlet pressure measurement device 10 are used to measure the respective pressures to thereby determine the pressure loss. The FBS solution 6 which is ready for passing through the column is kept in a constant temperature water bath 11 at a constant temperature of 37° C. In addition, a constant temperature water bath 11 is kept at constant temperature using a heater 12. For a circuit 13, a commercially available blood circuit can be used.

The ability of the column for adsorption can be evaluated by, for example, a column circulation test using the adsorption rate of IL-8, which is a type of organic matter, as an index. To an FBS solution used in the pressure loss measurement test, IL-8 is added in advance in such an amount that the concentration is 2000 pg/mL, and after a liquid passage for 2 hours, the concentration of IL-8 in the FBS solution is measured by enzyme-linked immunosorbent assay (ELISA). From the reduction rate from 2000 pg/mL, the IL-8 circulation adsorption rate can be obtained. For example, when the concentration of IL-8 in the FBS solution after the liquid passage for 2 hours is 500 pg/mL, 100×(2000 pg/mL−500 pg/mL)÷2000 pg/mL=75% is the IL-8 circulation adsorption rate.

During the adsorption treatment using the carrier for adsorbing organic matter of the present embodiment, if the strength of the carrier for adsorbing organic matter is insufficient, the fiber surface is peeled as fine particles due to brittle fracture caused by friction with the liquid, and these fine particles get mixed in the solution that has passed. Therefore, the purpose of collecting the adsorbed organic matter and separating and removing the organic matter from the liquid cannot be achieved. In particular, when the carrier for adsorbing organic matter is used for extracorporeal circulation, the generated fine particles may be mixed into the body. In this case, a separate filter must be installed to ensure safety, and thus the management becomes complicated. Therefore, it is desirable that the carrier for adsorbing organic matter is not subjected to brittle fracture as much as possible during circulation. The occurrence of the brittle fracture can be evaluated by measuring the amount of fine particles generated from the carrier for adsorbing organic matter.

As a method for evaluating the amount of fine particles generated from the carrier for adsorbing organic matter, a certain area of the carrier for adsorbing organic matter is cut out and filled in a cell, the water in the cell is stirred to extract the fine particles, and then the amount of the fine particles thus obtained by extraction is measured. When the carrier for adsorbing organic matter is subjected to brittle fracture during the use and fine particles are generated from the carrier, the fine particles may be mixed in the liquid that has passed. Thus, the carrier cannot be appropriately used as a carrier for adsorbing organic matter. Therefore, the amount of the generated fine particles is preferably 20 particles or less per 1 mL of water used for extraction of 0.01 $cm^3$ of the carrier for adsorbing organic matter. In particular, when the carrier for adsorbing organic matter is used for adsorbing blood components, in cases where the number of generated fine particles is 20 particles or less, the same level of safety as that of water for injection can be ensured. In this case, the carrier for adsorbing organic matter can be particularly preferably used for extracorporeal circulation and the like.

EXAMPLES

The carrier for adsorbing organic matter according to the present invention will now be specifically described with reference to Examples, but the present invention is not to be limited to these examples.

(Preparation of Fiber A)

A 32-island sea-island type solid composite fiber described in Description of U.S. Pat. No. 5,293,599 B2, wherein the islands were further core-sheath composites (hereinafter, Fiber A), was obtained using the following components under yarn-making conditions including a spinning rate of 800 m/minute.

Core component of island: polypropylene

Sheath component of island: polystyrene and polypropylene kneaded at a ratio of 90 wt % and 10 wt % respectively Sea component: copolyester whose main repeating unit is an ethylene terephthalate unit and which contains 3 wt % of 5-sodium sulfoisophthalic acid as a copolymerization component (hereinafter, PETIFA)

Composite ratio (weight ratio): core component of island: sheath component of island:sea component=41.5:33.5:25

Single fineness: 8.0 dtex (fiber diameter: 32 μm)

(Preparation of Fiber B)

A 32-island sea-island type solid composite fiber described in Description of U.S. Pat. No. 5,293,599 B2, wherein the islands were further core-sheath composites (hereinafter, Fiber B), was obtained using the following components under yarn-making conditions including a spinning rate of 800 m/minute.

Core component of island: polypropylene

Sheath component of island: polystyrene

Sea component: PETIFA

Composite ratio (weight ratio): core component of island: sheath component of island:sea component=41.5:33.5:25

Single fineness: 8.0 dtex (fiber diameter: 32 μm)

(Preparation of Fiber C)

A 32-island sea-island type solid composite fiber described in Description of U.S. Pat. No. 5,293,599 B2, wherein the islands were further core-sheath composites (hereinafter, Fiber C), was obtained using the following components under yarn-making conditions including a spinning rate of 800 m/minute.

Core component of island: polypropylene

Sheath component of island: polystyrene and polypropylene kneaded at a ratio of 90 wt % and 10 wt % respectively Sea component: PETIFA Composite ratio (weight ratio): core component of island: sheath component of island:sea component=65:10:25

Single fineness: 68.3 dtex (fiber diameter: 94 μm)

(Preparation of Fiber D)

Polystyrene as a sea component and polypropylene as an island component were separately melted and metered, and flowed into a spinning pack which integrated a sea-island composite spinneret in which 704 distribution holes for the island component were formed per discharge hole. This sea-island composite flow was then melt-discharged. The island ratio was controlled to 50 wt %, the distance from the surface of the sea-island type solid composite fiber to the outermost island component was adjusted to 2 μm. Thus, a sea-island type solid composite fiber (hereinafter, Fiber D) having a single fineness of 1.6 dtex (fiber diameter: 15 μm) was collected.

(Preparation of Fiber E)

A compatible mixture of 90 wt % of polystyrene and 10 wt % of syndiotactic polystyrene as a sea component and polypropylene as an island component were separately melted and metered, and flowed into a spinning pack which integrated a sea-island composite spinneret in which 704 distribution holes for the island component were formed per discharge hole. This sea-island composite flow was then melt-discharged. The island ratio was controlled to 50 wt %, the distance from the surface of the sea-island type solid composite fiber to the outermost island component was adjusted to 1 μm. Thus, a sea-island type solid composite fiber (hereinafter, Fiber F) having a single fineness of 3.0 dtex (fiber diameter: 20 μm) was collected.

(Preparation of Fiber F)

Syndiotactic polystyrene as a sea component and polypropylene as an island component were separately melted and metered, and flowed into a spinning pack which integrated a sea-island composite spinneret in which 704 distribution holes for the island component were formed per discharge hole. This sea-island composite flow was then melt-discharged. The island ratio was controlled to 50 wt %, the distance from the surface of the sea-island type solid composite fiber to the outermost island component was adjusted to 2 μm. Thus, a sea-island type solid composite fiber (hereinafter, Fiber F) having a single fineness of 7.1 dtex (fiber diameter: 30 μm) was collected.

(Preparation of Fiber G)

Polystyrene as a sea component and polypropylene as an island component were separately melted and metered, and flowed into a spinning pack which integrated a sea-island composite spinneret in which 704 distribution holes for the island component were formed per discharge hole. This sea-island composite flow was then melt-discharged. The island ratio was controlled to 50 wt %, the distance from the surface of the sea-island type solid composite fiber to the outermost island component was adjusted to 2 μm. Thus, a sea-island type solid composite fiber (hereinafter, Fiber G) having a single fineness of 3.0 dtex (fiber diameter: 20 μm) was collected.

(Preparation of Fiber H)

Polystyrene as a sea component and polypropylene as an island component were separately melted and metered, and flowed into a spinning pack which integrated a sea-island composite spinneret in which 704 distribution holes for the island component were formed per discharge hole. This sea-island composite flow was then melt-discharged. The island ratio was controlled to 20 wt %, the distance from the surface of the sea-island type solid composite fiber to the outermost island component was adjusted to 5 μm. Thus, a sea-island type solid composite fiber (hereinafter, Fiber H) having a single fineness of 3.0 dtex (fiber diameter: 20 μm) was collected.

(Preparation of Fiber I)

Polystyrene as a sea component and polypropylene as an island component were separately melted and metered, and flowed into a spinning pack which integrated a sea-island composite spinneret in which 704 distribution holes for the island component were formed per discharge hole. This sea-island composite flow was then melt-discharged. The island ratio was controlled to 50 wt %, the distance from the surface of the sea-island type solid composite fiber to the outermost island component was adjusted to 2 μm. Thus, a sea-island type solid composite fiber (hereinafter, Fiber I) having a single fineness of 9.0 dtex (fiber diameter: 34 μm) was collected.

(Preparation of Fiber J)

Polystyrene as a sea component and polypropylene as an island component were separately melted and metered, and flowed into a spinning pack which integrated a sea-island composite spinneret in which 704 distribution holes for the island component were formed per discharge hole. This sea-island composite flow was then melt-discharged. The island ratio was controlled to 50 wt %, the distance from the surface of the sea-island type solid composite fiber to the outermost island component was adjusted to 2 μm. Thus, a sea-island type solid composite fiber (hereinafter, Fiber J) having a single fineness of 12.0 dtex (fiber diameter: 40 μm) was collected.

(Preparation of Fiber K)

Polystyrene as a sea component and polypropylene as an island component were separately melted and metered, and flowed into a spinning pack which integrated a sea-island composite spinneret in which 210 distribution holes for the island component were formed per discharge hole. This sea-island composite flow was then melt-discharged. The island ratio was controlled to 50 wt %, the distance from the surface of the sea-island type solid composite fiber to the outermost island component was adjusted to 2 μm. Thus, a sea-island type solid composite fiber (hereinafter, Fiber K) having a single fineness of 3.0 dtex (fiber diameter: 20 μm) was collected.

(Preparation of Fiber L)

Polystyrene as a sea component and polypropylene as an island component were separately melted and metered, and flowed into a spinning pack which integrated a sea-island composite spinneret in which 165 distribution holes for the island component were formed per discharge hole. This sea-island composite flow was then melt-discharged. The island ratio was controlled to 50 wt %, the distance from the surface of the sea-island type solid composite fiber to the outermost island component was adjusted to 2 μm. Thus, a sea-island type solid composite fiber (hereinafter. Fiber L) having a single fineness of 3.0 dtex (fiber diameter: 20 μm) was collected.

(Preparation of Fiber M)

Polystyrene as a sea component and polypropylene as an island component were separately melted and metered, and flowed into a spinning pack which integrated a sea-island composite spinneret in which 67 distribution holes for the island component were formed per discharge hole. This sea-island composite flow was then melt-discharged. The island ratio was controlled to 50 wt %, the distance from the surface of the sea-island type solid composite fiber to the outermost island component was adjusted to 2 μm. Thus, a sea-island type solid composite fiber (hereinafter, Fiber M) having a single fineness of 3.0 dtex (fiber diameter: 20 μm) was collected.

(Preparation of Knitted Fabric A)

Fiber A was made into a circular knitting using a circular knitting machine (machine name: a circular knitting machine, MR-1, made by Maruzen Sangyo Co., Ltd.) and further impregnated with a 3 wt % sodium hydroxide aqueous solution at 95° C. for 8 hours to hydrolyze PETIFA of the sea component. Fabric A after hydrolysis was washed with water until the fabric became neutral and then dried. Thus, PETIFA of the sea component was completely removed and there only remained the island component of the core-sheath type solid fiber. This treatment resulted in a circularly knitted fabric A which was composed of a core-sheath type solid fiber having a single fineness of 0.2 dtex (fiber diameter: 5 μm) and which had a basis weight of 0.0046 g/cm$^2$ and a bulk density of 0.4 g/cm$^3$ (hereinafter, Knitted Fabric A).

(Preparation of Knitted Fabric B)

The same operation as in the preparation of Knitted Fabric A was carried out except that Fabric B was used instead of Fabric A to prepare a circularly knitted fabric B which was composed of a core-sheath type solid fiber having a single fineness of 0.2 dtex (fiber diameter: 5 μm) and which had a basis weight of 0.0046 g/cm$^2$ and a bulk density of 0.4 g/cm$^3$ (hereinafter, Knitted Fabric B).

(Preparation of Knitted Fabric C)

The same operation as in the preparation of Knitted Fabric A was carried out except that Fabric C was used instead of Fabric A to prepare a circularly knitted fabric C which was composed of a core-sheath type solid fiber having a single fineness of 1.6 dtex (fiber diameter: 15 μm) and which had a basis weight of 0.0046 g/cm$^2$ and a bulk density of 0.4 g/cm$^3$ (hereinafter, Knitted Fabric C).

(Preparation of Knitted Fabric D)

Fiber D was used and the density adjustment scale of a circular knitting machine (machine name: a circular knitting machine, MR-1, made by Maruzen Sangyo Co., Ltd.) was adjusted to prepare a circularly knitted fabric D having a basis weight of 0.0039 g/cm$^2$ and a bulk density of 0.22 g/cm$^3$ (hereinafter, Knitted Fabric D).

(Preparation of Knitted Fabric E)

Fiber E was used and the density adjustment scale of a circular knitting machine (machine name: a circular knitting machine, MR-1, made by Maruzen Sangyo Co., Ltd.) was adjusted to prepare a circularly knitted fabric E having a basis weight of 0.0039 g/cm$^2$ and a bulk density of 0.22 g/cm$^3$ (hereinafter, Knitted Fabric E).

(Preparation of Knitted Fabric F)

Fiber F was used and the density adjustment scale of a circular knitting machine (machine name: a circular knitting machine, MR-1, made by Maruzen Sangyo Co., Ltd.) was adjusted to prepare a circularly knitted fabric F having a basis weight of 0.0039 g/cm$^2$ and a bulk density of 0.22 g/cm$^3$ (hereinafter, Knitted Fabric F).

(Preparation of Knitted Fabric G)

Fiber G was used and the density adjustment scale of a circular knitting machine (machine name: a circular knitting machine, MR-1, made by Maruzen Sangyo Co., Ltd.) was adjusted to prepare a circularly knitted fabric G having a basis weight of 0.0039 g/cm$^2$ and a bulk density of 0.22 g/cm$^3$ (hereinafter, Knitted Fabric G).

(Preparation of Knitted Fabric H)

Fiber H was used and the density adjustment scale of a circular knitting machine (machine name: a circular knitting machine, MR-1, made by Maruzen Sangyo Co., Ltd.) was adjusted to prepare a circularly knitted fabric H having a basis weight of 0.0039 g/cm$^2$ and a bulk density of 0.22 g/cm$^3$ (hereinafter, Knitted Fabric H).

(Preparation of Knitted Fabric I)

Fiber I was used and the density adjustment scale of a circular knitting machine (machine name: a circular knitting machine, MR-1, made by Maruzen Sangyo Co., Ltd.) was adjusted to prepare a circularly knitted fabric I having a basis weight of 0.0039 g/cm$^2$ and a bulk density of 0.22 g/cm$^3$ (hereinafter, Knitted Fabric I).

(Preparation of Knitted Fabric J)

Fiber J was used and the density adjustment scale of a circular knitting machine (machine name: a circular knitting machine, MR-1, made by Maruzen Sangyo Co., Ltd.) was adjusted to prepare a circularly knitted fabric J having a basis weight of 0.0039 g/cm$^2$ and a bulk density of 0.22 g/cm$^3$ (hereinafter, Knitted Fabric J).

(Preparation of Knitted Fabric K)

Fiber K was used and the density adjustment scale of a circular knitting machine (machine name: a circular knitting machine, MR-1, made by Maruzen Sangyo Co., Ltd.) was adjusted to prepare a circularly knitted fabric K having a basis weight of 0.0039 g/cm$^2$ and a bulk density of 0.22 g/cm$^3$ (hereinafter, Knitted Fabric K).

(Preparation of Knitted Fabric L)

Fiber L was used and the density adjustment scale of a circular knitting machine (machine name: a circular knitting machine, MR-1, made by Maruzen Sangyo Co., Ltd.) was adjusted to prepare a circularly knitted fabric L having a basis weight of 0.0039 g/cm$^2$ and a bulk density of 0.22 g/cm$^3$ (hereinafter, Knitted Fabric L).

(Preparation of Knitted Fabric M)

Fiber M was used and the density adjustment scale of a circular knitting machine (machine name: a circular knitting machine, MR-1, made by Maruzen Sangyo Co., Ltd.) was adjusted to prepare a circularly knitted fabric M having a basis weight of 0.0039 g/cm$^2$ and a bulk density of 0.22 g/cm$^3$ (hereinafter, Knitted Fabric M).

(Preparation of Carrier for Adsorbing Organic Matter 1)

N-hydroxymethyl-2-chloroacetamide (hereinafter, NMCA) in an amount of 2.3 g was added to a solution mixture of 31 g of nitrobenzene and 31 g of 98 wt % sulfuric acid, and the resulting mixture was stirred at 10° C. until the NMCA was dissolved in the solution, to obtain an NMCA solution. Then, 0.2 g of paraformaldehyde (hereinafter, PFA) was added to a solution mixture of 2.0 g of nitrobenzene and 2.0 g of 98 wt % sulfuric acid, and the resulting mixture was stirred at 20° C. until the PFA was dissolved in the solution, to obtain a PFA solution. The PFA solution in an amount of 4.2 g was cooled to 5° C. and mixed with 64.3 g of the NMCA solution, the resulting mixture was stirred for 5 minutes, 1 g of Knitted Fabric A was added to the mixture to be impregnated with the mixture for 2 hours. The impregnated Knitted Fabric A was immersed in 200 mL of 0° C. nitrobenzene to thereby terminate the reaction, and the nitrobenzene adhering to the Knitted Fabric was washed with methanol.

Tetraethylenepentamine (hereinafter, TEPA) in an amount of 0.24 g and triethylamine in an amount of 2.1 g were dissolved in 51 g of DMSO, and to this solution, the Knitted Fabric A washed with methanol was added as it was. The Fabric was impregnated with the solution at 40° C. for 3 hours. The Knitted Fabric was collected on a glass filter by filtration, and washed with 500 mL of DMSO.

To 47 g of DMSO that was preliminarily dried by dehydration with activated molecular sieves 3A, 0.075 g of p-chlorophenyl isocyanate was added under a nitrogen atmosphere, the resulting mixture was heated to 30° C., and all the amount of the washed Knitted Fabric A was impregnated with the mixture for 1 hour. The Knitted Fabric was collected on a glass filter by filtration to obtain Knitted Fabric 1 which was a carrier for adsorbing organic matter (hereinafter, Carrier for Adsorbing Organic Matter 1).

Fiber Diameter Measurement of Sea-island Type Solid Composite Fibers Contained in Carrier for Adsorbing Organic Matter 1:

First, Carrier for Adsorbing Organic Matter 1 was frozen and embedded, and a cross section perpendicular to the fiber axis direction of the sea-island type solid composite fibers contained in the Carrier for Adsorbing Organic Matter 1 was prepared by a microtome. The obtained surface for observation was subjected to a conductivity treatment and used as an observation sample. The cross section of the observation sample was randomly observed using a field emission scanning electron microscope S-5500 manufactured by Hitachi High-Technologies, and 100 cross-sectional images were photographed. A minimum enclosing circle was created on a fiber cross section in the obtained cross-sectional images, and the diameter of the minimum enclosing circle was calculated. This operation was performed for all the 100 cross-sectional images, and the average value of the obtained diameters was used as the fiber diameter. The results are shown in Table 1.

Pore Volume Measurement of Sea-Island Type Solid Composite Fibers Contained in Carrier for Adsorbing Organic Matter 1:

About 6 mg of Carrier for Adsorbing Organic Matter 1 impregnated with water was taken out immediately before the DSC measurement, and after the excess water adhering to the surface was removed, the Carrier for Adsorbing Organic Matter 1 was enclosed in an aluminium sealed sample container. Using a DSC Q100 manufactured by TA Instruments, the Carrier for Adsorbing Organic Matter 1 was rapidly cooled to −55° C. in the wet state and then heated to 5° C. with a temperature increment of 0.3° C./min to measure the differential scanning calorific value, and using the peak top temperature as the melting point, a DSC curve was obtained. Pure water was used for temperature and calorific value calibration. From the obtained DSC curve, the pore volume of the sea-island type solid composite fibers contained in the Carrier for Adsorbing Organic Matter 1 was calculated according to the method of Ishikiriyama et al. (JOURNAL OF COLLOID AND INTERFACE SCIENCE, 1995, volume 171, pages 92-102 and pages 103-111). The results are shown in Table 1.

Basic Functional Group Content Measurement of Sea-Island Type Solid Composite Fibers Contained in Carrier for Adsorbing Organic Matter 1:

The basic functional group content of the sea-island type solid composite fibers contained in Carrier for Adsorbing Organic Matter 1 was measured by acid-base back titration of the basic functional group of the sea-island type solid composite fibers. Since the Carrier for Adsorbing Organic Matter 1 did not contain a reinforcing material, the weight of the Carrier for Adsorbing Organic Matter 1 was considered as the weight of the sea-island type solid composite fibers in the measurement. Carrier for Adsorbing Organic Matter 1 in an amount of 1.5 g placed in a 200-mL round-bottomed flask was left to stand at 80° C. for 48 hours in a dryer. Thus, Carrier for Adsorbing Organic Matter 1 subjected to a drying treatment was obtained. Then, to a polypropylene container, 1.0 g of the foregoing Carrier for Adsorbing Organic Matter 1 and 50 mL of a 6 M sodium hydroxide aqueous solution were added, the resultant was stirred for 30 minutes, and Carrier for Adsorbing Organic Matter 1 was collected by filtration using a paper filter. Then, the filtrated Carrier for Adsorbing Organic Matter 1 was added to 50 mL of ion-exchanged water, and the resultant was stirred for 30 minutes and the filtrated through a filter paper. The addition of the Carrier for Adsorbing Organic Matter 1 to ion-exchanged water and filtration of the Carrier for Adsorbing Organic Matter 1 were repeated until the pH of the ion-exchanged water reached 7 to obtain the desalted Carrier for Adsorbing Organic Matter 1. After the desalted Carrier for Adsorbing Organic Matter 1 was left to stand at 80° C. under normal pressure conditions for 48 hours, 1.0 g of the Carrier for Adsorbing Organic Matter 1 and 30 mL of 0.1 M hydrochloric acid were added to a polypropylene container and the resultant solution was stirred for 10 minutes. After the stirring, 5 mL of the solution alone was pulled out and transferred into a polypropylene container. Then, to the obtained solution, 0.1 mL of a 0.1 M sodium hydroxide aqueous solution was added dropwise. After dropwise addition, the resulting solution was stirred for 10 minutes, and the pH of the solution was measured. The same operation of dropwise addition, 10-minute stirring, and pH measurement was repeated 100 times. The amount of the sodium hydroxide aqueous solution added dropwise until the pH of the solution exceeded 8.5 was regarded as a titer per 1 g. The basic functional group content per 1 g of the sea-island type solid composite fibers contained in the Carrier for Adsorbing Organic Matter 1 was calculated using the titer per 1 g and the following Equation 2. The results are shown in Table 1.

Basic Functional Group Content per 1 g Dry Weight of Sea-Island Type Solid Composite Fibers Contained in Carrier for Adsorbing Organic Matter 1 (mmol/g)={Added 0.1 M Hydrochloric Acid Liquid Amount (30 mL)/Pulled-Out Hydrochloric Acid Liquid Amount (5 mL)}× Titer per 1 g (mL/g)×Sodium Hydroxide Aqueous Solution Concentration (0.1 mol/L)   Equation 2

Measurement of Distance from Surface of Sea-Island Type Solid Composite Fiber to Outermost Island Component in Sea-Island Type Solid Composite Fibers Contained in Carrier for Adsorbing Organic Matter 1:

First, Carrier for Adsorbing Organic Matter 1 was frozen and embedded, and a cross section perpendicular to the fiber axis direction of the sea-island type solid composite fibers contained in the Carrier for Adsorbing Organic Matter 1 was prepared by a microtome. The obtained surface for observation was subjected to a conductivity treatment and used as an observation sample. Images at 10 positions randomly selected were photographed at a magnification at which the island components could be clearly observed, using a field emission scanning electron microscope S-5500 manufactured by Hitachi High-Technologies. In each of the obtained 10 images, a randomly-selected sea-island type solid composite fiber was divided into six parts by 60 degrees (chain double-dashed line in FIG. 2) from the center of the minimum enclosing circle of the fiber cross-sectional image, and the shortest distance from the fiber surface to the outermost island component (d1 in FIG. 2) in each divided fiber cross section was measured in μm to one decimal place. When an island component protruded from the fiber surface, the distance was 0.0 μm (d2 in FIG. 2). When an island component spanned a plurality of divided fiber cross sections and the island component was the outermost island component in the plurality of divided fiber cross sections, the shortest distance from the fiber surface to the island component in each of the divided fiber cross sections (d4, d5 in FIG. 2) was measured. The average value of the distances measured as described above in each of the divided fiber cross sections (for example, the average value of d1, d2, d3, d4, d5, and d6 in FIG. 2) was calculated for all the 10 images, and the average value thus obtained was defined as the distance from the surface of the sea-island type solid composite fiber to the outermost island component. The results are shown in Table 1.

Measurement of Maximum Island Diameter of Island Components of Sea-Island Type Solid Composite Fibers Contained in Carrier for Adsorbing Organic Matter 1:

First, Carrier for Adsorbing Organic Matter 1 was frozen and embedded, and a cross section perpendicular to the fiber axis direction of the sea-island type solid composite fibers contained in the Carrier for Adsorbing Organic Matter 1 was prepared by a microtome. The obtained surface for observation was subjected to a conductivity treatment and used as an observation sample. Images at 10 positions randomly selected were photographed at a magnification at which the island components could be clearly observed, using a field emission scanning electron microscope S-5500 manufactured by Hitachi High-Technologies. In the 10 images thus obtained, a minimum enclosing circle was created on an island component randomly selected, and the diameter of the minimum enclosing circle was calculated and used as the island diameter. This operation was performed on all the 100 images of the selected island components, and the largest island diameter was defined as the maximum island diameter of the island component of the sea-island type solid composite fiber. The results are shown in Table 1.

(Preparation of Carrier for Adsorbing Organic Matter 2)

The same operation as for Carrier for Adsorbing Organic Matter 1 was carried out except that Knitted Fabric B was used instead of Knitted Fabric A, to obtain Knitted Fabric 2 which was a carrier for adsorbing organic matter (hereinafter, Carrier for Adsorbing Organic Matter 2).

Fiber Diameter Measurement of Sea-Island Type Solid Composite Fibers Contained in Carrier for Adsorbing Organic Matter 2:

The same operation as for the Carrier for Adsorbing Organic Matter 1 was carried out, and the fiber diameter of the sea-island type solid composite fibers contained in the Carrier for Adsorbing Organic Matter 2 was measured. The results are shown in Table 1.

Pore Volume Measurement of Sea-Island Type Solid Composite Fibers Contained in Carrier for Adsorbing Organic Matter 2:

The same operation as for the Carrier for Adsorbing Organic Matter 1 was carried out, and the pore volume of the sea-island type solid composite fibers contained in the Carrier for Adsorbing Organic Matter 2 was measured. The results are shown in Table 1.

Basic Functional Group Content Measurement of Sea-Island Type Solid Composite Fibers Contained in Carrier for Adsorbing Organic Matter 2:

The same operation as for the Carrier for Adsorbing Organic Matter 1 was carried out, and the basic functional group content of the sea-island type solid composite fibers contained in the Carrier for Adsorbing Organic Matter 2 was measured. The results are shown in Table 1.

Measurement of Distance from Surface of Sea-Island Type Solid Composite Fiber to Outermost Island Component in Sea-Island Type Solid Composite Fibers Contained in Carrier for Adsorbing Organic Matter 2:

The same operation as for the Carrier for Adsorbing Organic Matter 1 was carried out, and the distance from the surface of a sea-island type solid composite fiber to the outermost island component in the sea-island type solid composite fibers contained in the Carrier for Adsorbing Organic Matter 2 was measured. The results are shown in Table 1.

Measurement of Maximum Island Diameter of Island Components of Sea-Island Type Solid Composite Fibers Contained in Carrier for Adsorbing Organic Matter 2:

The same operation as for the Carrier for Adsorbing Organic Matter 1 was carried out, and the maximum island diameter of the island components in sea-island type solid composite fibers contained in the Carrier for Adsorbing Organic Matter 2 was measured. The results are shown in Table 1.

(Preparation of Carrier for Adsorbing Organic Matter 3)

The same operation as for Carrier for Adsorbing Organic Matter 1 was carried out except that Knitted Fabric C was used instead of Knitted Fabric A, to obtain Knitted Fabric 3 which was a carrier for adsorbing organic matter (hereinafter, Carrier for Adsorbing Organic Matter 3).

Fiber Diameter Measurement of Sea-Island Type Solid Composite Fibers Contained in Carrier for Adsorbing Organic Matter 3:

The same operation as for the Carrier for Adsorbing Organic Matter 1 was carried out, and the fiber diameter of the sea-island type solid composite fibers contained in the Carrier for Adsorbing Organic Matter 3 was measured. The results are shown in Table 1.

Pore Volume Measurement of Sea-Island Type Solid Composite Fibers Contained in Carrier for Adsorbing Organic Matter 3:

The same operation as for the Carrier for Adsorbing Organic Matter 1 was carried out, and the pore volume of the sea-island type solid composite fibers contained in the Carrier for Adsorbing Organic Matter 3 was measured. The results are shown in Table 1.

Basic Functional Group Content Measurement of Sea-Island Type Solid Composite Fibers Contained in Carrier for Adsorbing Organic Matter 3:

The same operation as for the Carrier for Adsorbing Organic Matter 1 was carried out, and the basic functional group content of the sea-island type solid composite fibers contained in the Carrier for Adsorbing Organic Matter 3 was measured. The results are shown in Table 1.

Measurement of Distance from Surface of Sea-Island Type Solid Composite Fiber to Outermost Island Component in Sea-Island Type Solid Composite Fibers Contained in Carrier for Adsorbing Organic Matter 3:

The same operation as for the Carrier for Adsorbing Organic Matter 1 was carried out, and the distance from the surface of a sea-island type solid composite fiber to the outermost island component in the sea-island type solid composite fibers contained in the Carrier for Adsorbing Organic Matter 3 was measured. The results are shown in Table 1.

Measurement of Maximum Island Diameter of Island Components of Sea-Island Type Solid Composite Fibers Contained in Carrier for Adsorbing Organic Matter 3:

The same operation as for the Carrier for Adsorbing Organic Matter 1 was carried out, and the maximum island diameter of the island components in sea-island type solid composite fibers contained in the Carrier for Adsorbing Organic Matter 3 was measured. The results are shown in Table 1.

(Preparation of Carrier for Adsorbing Organic Matter 4)

The same operation as for Carrier for Adsorbing Organic Matter 1 was carried out except that Knitted Fabric D was used instead of Knitted Fabric A, to obtain Knitted Fabric 4 which was a carrier for adsorbing organic matter (hereinafter, Carrier for Adsorbing Organic Matter 4).

Fiber Diameter Measurement of Sea-Island Type Solid Composite Fibers Contained in Carrier for Adsorbing Organic Matter 4:

The same operation as for the Carrier for Adsorbing Organic Matter 1 was carried out, and the fiber diameter of the sea-island type solid composite fibers contained in the Carrier for Adsorbing Organic Matter 4 was measured. The results are shown in Table 1.

Pore Volume Measurement of Sea-Island Type Solid Composite Fibers Contained in Carrier for Adsorbing Organic Matter 4:

The same operation as for the Carrier for Adsorbing Organic Matter 1 was carried out, and the pore volume of the sea-island type solid composite fibers contained in the Carrier for Adsorbing Organic Matter 4 was measured. The results are shown in Table 1.

Basic Functional Group Content Measurement of Sea-Island Type Solid Composite Fibers Contained in Carrier for Adsorbing Organic Matter 4:

The same operation as for the Carrier for Adsorbing Organic Matter 1 was carried out, and the basic functional group content of the sea-island type solid composite fibers contained in the Carrier for Adsorbing Organic Matter 4 was measured. The results are shown in Table 1.

Measurement of Distance from Surface of Sea-Island Type Solid Composite Fiber to Outermost Island Component in Sea-Island Type Solid Composite Fibers Contained in Carrier for Adsorbing Organic Matter 4:

The same operation as for the Carrier for Adsorbing Organic Matter 1 was carried out, and the distance from the surface of a sea-island type solid composite fiber to the outermost island component in the sea-island type solid composite fibers contained in the Carrier for Adsorbing Organic Matter 4 was measured. The results are shown in Table 1.

Measurement of Maximum Island Diameter of Island Components of Sea-Island Type Solid Composite Fibers Contained in Carrier for Adsorbing Organic Matter 4:

The same operation as for the Carrier for Adsorbing Organic Matter 1 was carried out, and the maximum island diameter of the island components in sea-island type solid composite fibers contained in the Carrier for Adsorbing Organic Matter 4 was measured. The results are shown in Table 1.

(Preparation of Carrier for Adsorbing Organic Matter 5)

The same operation as for Carrier for Adsorbing Organic Matter 1 was carried out except that Knitted Fabric E was used instead of Knitted Fabric A, to obtain Knitted Fabric 5 which was a carrier for adsorbing organic matter (hereinafter, Carrier for Adsorbing Organic Matter 5).

Fiber Diameter Measurement of Sea-Island Type Solid Composite Fibers Contained in Carrier for Adsorbing Organic Matter 5:

The same operation as for the Carrier for Adsorbing Organic Matter 1 was carried out, and the fiber diameter of the sea-island type solid composite fibers contained in the Carrier for Adsorbing Organic Matter 5 was measured. The results are shown in Table 1.

Pore Volume Measurement of Sea-Island Type Solid Composite Fibers Contained in Carrier for Adsorbing Organic Matter 5:

The same operation as for the Carrier for Adsorbing Organic Matter 1 was carried out, and the pore volume of the sea-island type solid composite fibers contained in the Carrier for Adsorbing Organic Matter 5 was measured. The results are shown in Table 1.

Basic Functional Group Content Measurement of Sea-Island Type Solid Composite Fibers Contained in Carrier for Adsorbing Organic Matter 5:

The same operation as for the Carrier for Adsorbing Organic Matter 1 was earned out, and the basic functional group content of the sea-island type solid composite fibers contained in the Carrier for Adsorbing Organic Matter 5 was measured. The results are shown in Table 1.

Measurement of Distance from Surface of Sea-Island Type Solid Composite Fiber to Outermost Island Component in Sea-Island Type Solid Composite Fibers Contained in Carrier for Adsorbing Organic Matter 5:

The same operation as for the Carrier for Adsorbing Organic Matter 1 was carried out, and the distance from the surface of a sea-island type solid composite fiber to the outermost island component in the sea-island type solid composite fibers contained in the Carrier for Adsorbing Organic Matter 5 was measured. The results are shown in Table 1.

Measurement of Maximum Island Diameter of Island Components of Sea-Island Type Solid Composite Fibers Contained in Carrier for Adsorbing Organic Matter 5:

The same operation as for the Carrier for Adsorbing Organic Matter 1 was carried out, and the maximum island diameter of the island components in sea-island type solid composite fibers contained in the Carrier for Adsorbing Organic Matter 5 was measured. The results are shown in Table 1.

(Preparation of Carrier for Adsorbing Organic Matter 6)

The same operation as for Carrier for Adsorbing Organic Matter 1 was carried out except that Knitted Fabric F was used instead of Knitted Fabric A, to obtain Knitted Fabric 6 which was a carrier for adsorbing organic matter (hereinafter, Carrier for Adsorbing Organic Matter 6).

Fiber Diameter Measurement of Sea-Island Type Solid Composite Fibers Contained in Carrier for Adsorbing Organic Matter 6:

The same operation as for the Carrier for Adsorbing Organic Matter 1 was carried out, and the fiber diameter of the sea-island type solid composite fibers contained in the Carrier for Adsorbing Organic Matter 6 was measured. The results are shown in Table 1.

Pore Volume Measurement of Sea-Island Type Solid Composite Fibers Contained in Carrier for Adsorbing Organic Matter 6:

The same operation as for the Carrier for Adsorbing Organic Matter 1 was carried out, and the pore volume of the sea-island type solid composite fibers contained in the Carrier for Adsorbing Organic Matter 6 was measured. The results are shown in Table 1.

Basic Functional Group Content Measurement of Sea-Island Type Solid Composite Fibers Contained in Carrier for Adsorbing Organic Matter 6:

The same operation as for the Carrier for Adsorbing Organic Matter 1 was carried out, and the basic functional group content of the sea-island type solid composite fibers contained in the Carrier for Adsorbing Organic Matter 6 was measured. The results are shown in Table 1.

Measurement of Distance from Surface of Sea-Island Type Solid Composite Fiber to Outermost Island Component in Sea-Island Type Solid Composite Fibers Contained in Carrier for Adsorbing Organic Matter 6:

The same operation as for the Carrier for Adsorbing Organic Matter 1 was carried out, and the distance from the surface of a sea-island type solid composite fiber to the outermost island component in the sea-island type solid composite fibers contained in the Carrier for Adsorbing Organic Matter 6 was measured. The results are shown in Table 1.

Measurement of Maximum Island Diameter of Island Components of Sea-Island Type Solid Composite Fibers Contained in Carrier for Adsorbing Organic Matter 6:

The same operation as for the Carrier for Adsorbing Organic Matter 1 was carried out, and the maximum island diameter of the island components in sea-island type solid composite fibers contained in the Carrier for Adsorbing Organic Matter 6 was measured. The results are shown in Table 1.

(Preparation of Carrier for Adsorbing Organic Matter 7)

The same operation as for Carrier for Adsorbing Organic Matter 1 was carried out except that Knitted Fabric G was used instead of Knitted Fabric A, to obtain Knitted Fabric 7 which was a carrier for adsorbing organic matter (hereinafter, Carrier for Adsorbing Organic Matter 7).

Fiber Diameter Measurement of Sea-Island Type Solid Composite Fibers Contained in Carrier for Adsorbing Organic Matter 7:

The same operation as for the Carrier for Adsorbing Organic Matter 1 was carried out, and the fiber diameter of the sea-island type solid composite fibers contained in the Carrier for Adsorbing Organic Matter 7 was measured. The results are shown in Table 1.

Pore Volume Measurement of Sea-Island Type Solid Composite Fibers Contained in Carrier for Adsorbing Organic Matter 7:

The same operation as for the Carrier for Adsorbing Organic Matter 1 was carried out, and the pore volume of the sea-island type solid composite fibers contained in the Carrier for Adsorbing Organic Matter 7 was measured. The results are shown in Table 1.

Basic Functional Group Content Measurement of Sea-Island Type Solid Composite Fibers Contained in Carrier for Adsorbing Organic Matter 7:

The same operation as for the Carrier for Adsorbing Organic Matter 1 was carried out, and the basic functional group content of the sea-island type solid composite fibers contained in the Carrier for Adsorbing Organic Matter 7 was measured. The results are shown in Table 1.

Measurement of Distance from Surface of Sea-Island Type Solid Composite Fiber to Outermost Island Component in Sea-Island Type Solid Composite Fibers Contained in Carrier for Adsorbing Organic Matter 7:

The same operation as for the Carrier for Adsorbing Organic Matter 1 was carried out, and the distance from the surface of a sea-island type solid composite fiber to the outermost island component in the sea-island type solid composite fibers contained in the Carrier for Adsorbing Organic Matter 7 was measured. The results are shown in Table 1.

Measurement of Maximum Island Diameter of Island Components of Sea-Island Type Solid Composite Fibers Contained in Carrier for Adsorbing Organic Matter 7:

The same operation as for the Carrier for Adsorbing Organic Matter 1 was carried out, and the maximum island diameter of the island components in sea-island type solid composite fibers contained in the Carrier for Adsorbing Organic Matter 7 was measured. The results are shown in Table 1.

(Preparation of Carrier for Adsorbing Organic Matter 8)

The same operation as for Carrier for Adsorbing Organic Matter 1 was carried out except that Knitted Fabric G was used instead of Knitted Fabric A and that the amount of TEPA was changed from 0.24 g to 0 g, to obtain Knitted Fabric 8 which was a carrier for adsorbing organic matter (hereinafter, Carrier for Adsorbing Organic Matter 8).

Fiber Diameter Measurement of Sea-Island Type Solid Composite Fibers Contained in Carrier for Adsorbing Organic Matter 8:

The same operation as for the Carrier for Adsorbing Organic Matter 1 was carried out, and the fiber diameter of the sea-island type solid composite fibers contained in the Carrier for Adsorbing Organic Matter 8 was measured. The results are shown in Table 1.

Pore Volume Measurement of Sea-Island Type Solid Composite Fibers Contained in Carrier for Adsorbing Organic Matter 8:

The same operation as for the Carrier for Adsorbing Organic Matter 1 was carried out, and the pore volume of the sea-island type solid composite fibers contained in the Carrier for Adsorbing Organic Matter 8 was measured. The results are shown in Table 1.

Basic Functional Group Content Measurement of Sea-Island Type Solid Composite Fibers Contained in Carrier for Adsorbing Organic Matter 8:

The same operation as for the Carrier for Adsorbing Organic Matter 1 was carried out, and the basic functional group content of the sea-island type solid composite fibers contained in the Carrier for Adsorbing Organic Matter 8 was measured. The results are shown in Table 1.

Measurement of Distance from Surface of Sea-Island Type Solid Composite Fiber to Outermost Island Component in Sea-Island Type Solid Composite Fibers Contained in Carrier for Adsorbing Organic Matter 8:

The same operation as for the Carrier for Adsorbing Organic Matter 1 was carried out, and the distance from the surface of a sea-island type solid composite fiber to the outermost island component in the sea-island type solid composite fibers contained in the Carrier for Adsorbing Organic Matter 8 was measured. The results are shown in Table 1.

Measurement of Maximum Island Diameter of Island Components of Sea-Island Type Solid Composite Fibers Contained in Carrier for Adsorbing Organic Matter 8:

The same operation as for the Carrier for Adsorbing Organic Matter 1 was carried out, and the maximum island diameter of the island components in sea-island type solid composite fibers contained in the Carrier for Adsorbing Organic Matter 8 was measured. The results are shown in Table 1.

(Preparation of Carrier for Adsorbing Organic Matter 9)

The same operation as for Carrier for Adsorbing Organic Matter 1 was carried out except that Knitted Fabric G was used instead of Knitted Fabric A and that the amount of NMCA was changed from 2.3 g to 6.9 g, to obtain Knitted Fabric 9 which was a carrier for adsorbing organic matter (hereinafter, Carrier for Adsorbing Organic Matter 9).

Fiber Diameter Measurement of Sea-Island Type Solid Composite Fibers Contained in Carrier for Adsorbing Organic Matter 9:

The same operation as for the Carrier for Adsorbing Organic Matter 1 was carried out, and the fiber diameter of the sea-island type solid composite fibers contained in the Carrier for Adsorbing Organic Matter 9 was measured. The results are shown in Table 1.

Pore Volume Measurement of Sea-Island Type Solid Composite Fibers Contained in Carrier for Adsorbing Organic Matter 9:

The same operation as for the Carrier for Adsorbing Organic Matter 1 was carried out, and the pore volume of the sea-island type solid composite fibers contained in the Carrier for Adsorbing Organic Matter 9 was measured. The results are shown in Table 1.

Basic Functional Group Content Measurement of Sea-Island Type Solid Composite Fibers Contained in Carrier for Adsorbing Organic Matter 9:

The same operation as for the Carrier for Adsorbing Organic Matter 1 was carried out, and the basic functional group content of the sea-island type solid composite fibers contained in the Carrier for Adsorbing Organic Matter 9 was measured. The results are shown in Table 1.

Measurement of Distance from Surface of Sea-Island Type Solid Composite Fiber to Outermost Island Component in Sea-Island Type Solid Composite Fibers Contained in Carrier for Adsorbing Organic Matter 9:

The same operation as for the Carrier for Adsorbing Organic Matter 1 was carried out, and the distance from the surface of a sea-island type solid composite fiber to the outermost island component in the sea-island type solid composite fibers contained in the Carrier for Adsorbing Organic Matter 9 was measured. The results are shown in Table 1.

Measurement of Maximum Island Diameter of Island Components of Sea-Island Type Solid Composite Fibers Contained in Carrier for Adsorbing Organic Matter 9:

The same operation as for the Carrier for Adsorbing Organic Matter 1 was carried out, and the maximum island diameter of the island components in sea-island type solid composite fibers contained in the Carrier for Adsorbing Organic Matter 9 was measured. The results are shown in Table 1.

(Preparation of Carrier for Adsorbing Organic Matter 10)

The same operation as for Carrier for Adsorbing Organic Matter 1 was carried out except that Knitted Fabric H was used instead of Knitted Fabric A, to obtain Knitted Fabric 10 which was a carrier for adsorbing organic matter (hereinafter, Carrier for Adsorbing Organic Matter 10).

Fiber Diameter Measurement of Sea-Island Type Solid Composite Fibers Contained in Carrier for Adsorbing Organic Matter 10:

The same operation as for the Carrier for Adsorbing Organic Matter 1 was carried out, and the fiber diameter of the sea-island type solid composite fibers contained in the Carrier for Adsorbing Organic Matter 10 was measured. The results are shown in Table 1.

Pore Volume Measurement of Sea-Island Type Solid Composite Fibers Contained in Carrier for Adsorbing Organic Matter 10:

The same operation as for the Carrier for Adsorbing Organic Matter 1 was carried out, and the pore volume of the sea-island type solid composite fibers contained in the Carrier for Adsorbing Organic Matter 10 was measured. The results are shown in Table 1.

Basic Functional Group Content Measurement of Sea-Island Type Solid Composite Fibers Contained in Carrier for Adsorbing Organic Matter 10:

The same operation as for the Carrier for Adsorbing Organic Matter 1 was carried out, and the basic functional group content of the sea-island type solid composite fibers contained in the Carrier for Adsorbing Organic Matter 10 was measured. The results are shown in Table 1.

Measurement of Distance from Surface of Sea-Island Type Solid Composite Fiber to Outermost Island Component in Sea-Island Type Solid Composite Fibers Contained in Carrier for Adsorbing Organic Matter 10:

The same operation as for the Carrier for Adsorbing Organic Matter 1 was carried out, and the distance from the surface of a sea-island type solid composite fiber to the outermost island component in the sea-island type solid composite fibers contained in the Carrier for Adsorbing Organic Matter 10 was measured. The results are shown in Table 1.

Measurement of Maximum Island Diameter of Island Components of Sea-Island Type Solid Composite Fibers Contained in Carrier for Adsorbing Organic Matter 10:

The same operation as for the Carrier for Adsorbing Organic Matter 1 was carried out, and the maximum island diameter of the island components in sea-island type solid composite fibers contained in the Carrier for Adsorbing Organic Matter 10 was measured. The results are shown in Table 1.

(Preparation of Carrier for Adsorbing Organic Matter 11)

The same operation as for Carrier for Adsorbing Organic Matter 1 was carried out except that Knitted Fabric I was used instead of Knitted Fabric A, to obtain Knitted Fabric 11 which was a carrier for adsorbing organic matter (hereinafter, Carrier for Adsorbing Organic Matter 11).

Fiber Diameter Measurement of Sea-Island Type Solid Composite Fibers Contained in Carrier for Adsorbing Organic Matter 11:

The same operation as for the Carrier for Adsorbing Organic Matter 1 was carried out, and the fiber diameter of the sea-island type solid composite fibers contained in the Carrier for Adsorbing Organic Matter 11 was measured. The results are shown in Table 1.

Pore Volume Measurement of Sea-Island Type Solid Composite Fibers Contained in Carrier for Adsorbing Organic Matter 11:

The same operation as for the Carrier for Adsorbing Organic Matter 1 was carried out, and the pore volume of the sea-island type solid composite fibers contained in the Carrier for Adsorbing Organic Matter 11 was measured. The results are shown in Table 1.

Basic Functional Group Content Measurement of Sea-Island Type Solid Composite Fibers Contained in Carrier for Adsorbing Organic Matter 11:

The same operation as for the Carrier for Adsorbing Organic Matter 1 was carried out, and the basic functional group content of the sea-island type solid composite fibers contained in the Carrier for Adsorbing Organic Matter 11 was measured. The results are shown in Table 1.

Measurement of Distance from Surface of Sea-Island Type Solid Composite Fiber to Outermost Island Component in Sea-Island Type Solid Composite Fibers Contained in Carrier for Adsorbing Organic Matter 11:

The same operation as for the Carrier for Adsorbing Organic Matter 1 was carried out, and the distance from the surface of a sea-island type solid composite fiber to the outermost island component in the sea-island type solid composite fibers contained in the Carrier for Adsorbing Organic Matter 11 was measured. The results are shown in Table 1.

Measurement of Maximum Island Diameter of Island Components of Sea-Island Type Solid Composite Fibers Contained in Carrier for Adsorbing Organic Matter 11:

The same operation as for the Carrier for Adsorbing Organic Matter 1 was carried out, and the maximum island diameter of the island components in sea-island type solid composite fibers contained in the Carrier for Adsorbing Organic Matter 11 was measured. The results are shown in Table 1.

(Preparation of Carrier for Adsorbing Organic Matter 12)

The same operation as for Carrier for Adsorbing Organic Matter 1 was carried out except that Knitted Fabric J was used instead of Knitted Fabric A, to obtain Knitted Fabric 12 which was a carrier for adsorbing organic matter (hereinafter, Carrier for Adsorbing Organic Matter 12).

Fiber Diameter Measurement of Sea-Island Type Solid Composite Fibers Contained in Carrier for Adsorbing Organic Matter 12:

The same operation as for the Carrier for Adsorbing Organic Matter 1 was carried out, and the fiber diameter of the sea-island type solid composite fibers contained in the Carrier for Adsorbing Organic Matter 12 was measured. The results are shown in Table 1.

Pore Volume Measurement of Sea-Island Type Solid Composite Fibers Contained in Carrier for Adsorbing Organic Matter 12:

The same operation as for the Carrier for Adsorbing Organic Matter 1 was carried out, and the pore volume of the sea-island type solid composite fibers contained in the Carrier for Adsorbing Organic Matter 12 was measured. The results are shown in Table 1.

Basic Functional Group Content Measurement of Sea-Island Type Solid Composite Fibers Contained in Carrier for Adsorbing Organic Matter 12:

The same operation as for the Carrier for Adsorbing Organic Matter 1 was carried out, and the basic functional group content of the sea-island type solid composite fibers contained in the Carrier for Adsorbing Organic Matter 12 was measured. The results are shown in Table 1.

Measurement of Distance from Surface of Sea-Island Type Solid Composite Fiber to Outermost Island Component in Sea-Island Type Solid Composite Fibers Contained in Carrier for Adsorbing Organic Matter 12:

The same operation as for the Carrier for Adsorbing Organic Matter 1 was carried out, and the distance from the surface of a sea-island type solid composite fiber to the outermost island component in the sea-island type solid composite fibers contained in the Carrier for Adsorbing Organic Matter 12 was measured. The results are shown in Table 1.

Measurement of Maximum Island Diameter of Island Components of Sea-Island Type Solid Composite Fibers Contained in Carrier for Adsorbing Organic Matter 12:

The same operation as for the Carrier for Adsorbing Organic Matter 1 was carried out, and the maximum island diameter of the island components in sea-island type solid composite fibers contained in the Carrier for Adsorbing Organic Matter 12 was measured. The results are shown in Table 1.

(Preparation of Carrier for Adsorbing Organic Matter 13)

The same operation as for Carrier for Adsorbing Organic Matter 1 was carried out except that Knitted Fabric K was used instead of Knitted Fabric A, to obtain Knitted Fabric 13 which was a carrier for adsorbing organic matter (hereinafter, Carrier for Adsorbing Organic Matter 13).

Fiber Diameter Measurement of Sea-Island Type Solid Composite Fibers Contained in Carrier for Adsorbing Organic Matter 13:

The same operation as for the Carrier for Adsorbing Organic Matter 1 was carried out, and the fiber diameter of the sea-island type solid composite fibers contained in the Carrier for Adsorbing Organic Matter 13 was measured. The results are shown in Table 1.

Pore Volume Measurement of Sea-Island Type Solid Composite Fibers Contained in Carrier for Adsorbing Organic Matter 13:

The same operation as for the Carrier for Adsorbing Organic Matter 1 was carried out, and the pore volume of the sea-island type solid composite fibers contained in the Carrier for Adsorbing Organic Matter 13 was measured. The results are shown in Table 1.

Basic Functional Group Content Measurement of Sea-Island Type Solid Composite Fibers Contained in Carrier for Adsorbing Organic Matter 13:

The same operation as for the Carrier for Adsorbing Organic Matter 1 was carried out, and the basic functional group content of the sea-island type solid composite fibers contained in the Carrier for Adsorbing Organic Matter 13 was measured. The results are shown in Table 1.

Measurement of Distance from Surface of Sea-Island Type Solid Composite Fiber to Outermost Island Component in Sea-Island Type Solid Composite Fibers Contained in Carrier for Adsorbing Organic Matter 13:

The same operation as for the Carrier for Adsorbing Organic Matter 1 was carried out, and the distance from the surface of a sea-island type solid composite fiber to the outermost island component in the sea-island type solid composite fibers contained in the Carrier for Adsorbing Organic Matter 13 was measured. The results are shown in Table 1.

Measurement of Maximum Island Diameter of Island Components of Sea-Island Type Solid Composite Fibers Contained in Carrier for Adsorbing Organic Matter 13:

The same operation as for the Carrier for Adsorbing Organic Matter 1 was carried out, and the maximum island diameter of the island components in sea-island type solid composite fibers contained in the Carrier for Adsorbing Organic Matter 13 was measured. The results are shown in Table 1.

(Preparation of Carrier for Adsorbing Organic Matter 14)

The same operation as for Carrier for Adsorbing Organic Matter 1 was carried out except that Knitted Fabric L was used instead of Knitted Fabric A, to obtain Knitted Fabric 14 which was a carrier for adsorbing organic matter (hereinafter, Carrier for Adsorbing Organic Matter 14).

Fiber Diameter Measurement of Sea-Island Type Solid Composite Fibers Contained in Carrier for Adsorbing Organic Matter 14:

The same operation as for the Carrier for Adsorbing Organic Matter 1 was carried out, and the fiber diameter of the sea-island type solid composite fibers contained in the Carrier for Adsorbing Organic Matter 14 was measured. The results are shown in Table 1.

Pore Volume Measurement of Sea-Island Type Solid Composite Fibers Contained in Carrier for Adsorbing Organic Matter 14:

The same operation as for the Carrier for Adsorbing Organic Matter 1 was carried out, and the pore volume of the sea-island type solid composite fibers contained in the Carrier for Adsorbing Organic Matter 14 was measured. The results are shown in Table 1.

Basic Functional Group Content Measurement of Sea-Island Type Solid Composite Fibers Contained in Carrier for Adsorbing Organic Matter 14:

The same operation as for the Carrier for Adsorbing Organic Matter 1 was carried out, and the basic functional group content of the sea-island type solid composite fibers contained in the Carrier for Adsorbing Organic Matter 14 was measured. The results are shown in Table 1.

Measurement of Distance from Surface of Sea-Island Type Solid Composite Fiber to Outermost Island Component in Sea-Island Type Solid Composite Fibers Contained in Carrier for Adsorbing Organic Matter 14:

The same operation as for the Carrier for Adsorbing Organic Matter 1 was carried out, and the distance from the surface of a sea-island type solid composite fiber to the outermost island component in the sea-island type solid composite fibers contained in the Carrier for Adsorbing Organic Matter 14 was measured. The results are shown in Table 1.

Measurement of Maximum Island Diameter of Island Components of Sea-Island Type Solid Composite Fibers Contained in Carrier for Adsorbing Organic Matter 14:

The same operation as for the Carrier for Adsorbing Organic Matter 1 was carried out, and the maximum island diameter of the island components in sea-island type solid composite fibers contained in the Carrier for Adsorbing Organic Matter 14 was measured. The results are shown in Table 1.

(Preparation of Carrier for Adsorbing Organic Matter 15)

The same operation as for Carrier for Adsorbing Organic Matter 1 was carried out except that Knitted Fabric M was used instead of Knitted Fabric A, to obtain Knitted Fabric 15 which was a carrier for adsorbing organic matter (hereinafter, Carrier for Adsorbing Organic Matter 15).

Fiber Diameter Measurement of Sea-Island Type Solid Composite Fibers Contained in Carrier for Adsorbing Organic Matter 15:

The same operation as for the Carrier for Adsorbing Organic Matter 1 was carried out, and the fiber diameter of the sea-island type solid composite fibers contained in the Carrier for Adsorbing Organic Matter 15 was measured. The results are shown in Table 1.

Pore Volume Measurement of Sea-Island Type Solid Composite Fibers Contained in Carrier for Adsorbing Organic Matter 15:

The same operation as for the Carrier for Adsorbing Organic Matter 1 was carried out, and the pore volume of the sea-island type solid composite fibers contained in the Carrier for Adsorbing Organic Matter 15 was measured. The results are shown in Table 1.

Basic Functional Group Content Measurement of Sea-Island Type Solid Composite Fibers Contained in Carrier for Adsorbing Organic Matter 15:

The same operation as for the Carrier for Adsorbing Organic Matter 1 was carried out, and the basic functional group content of the sea-island type solid composite fibers contained in the Carrier for Adsorbing Organic Matter 15 was measured. The results are shown in Table 1.

Measurement of Distance from Surface of Sea-Island Type Solid Composite Fiber to Outermost Island Component in Sea-Island Type Solid Composite Fibers Contained in Carrier for Adsorbing Organic Matter 15:

The same operation as for the Carrier for Adsorbing Organic Matter 1 was carried out, and the distance from the surface of a sea-island type solid composite fiber to the outermost island component in the sea-island type solid composite fibers contained in the Carrier for Adsorbing Organic Matter 15 was measured. The results are shown in Table 1.

Measurement of Maximum Island Diameter of Island Components of Sea-Island Type Solid Composite Fibers Contained in Carrier for Adsorbing Organic Matter 15:

The same operation as for the Carrier for Adsorbing Organic Matter 1 was carried out, and the maximum island diameter of the island components in sea-island type solid composite fibers contained in the Carrier for Adsorbing Organic Matter 15 was measured. The results are shown in Table 1.

(Preparation of Carrier for Adsorbing Organic Matter 16)

The same operation as for Carrier for Adsorbing Organic Matter 1 was carried out except that Knitted Fabric G was used instead of Knitted Fabric A and that the amount of TEPA was changed from 0.24 g to 0.10 g, to obtain Knitted Fabric 16 which was a carrier for adsorbing organic matter (hereinafter, Carrier for Adsorbing Organic Matter 16).

Fiber Diameter Measurement of Sea-Island Type Solid Composite Fibers Contained in Carrier for Adsorbing Organic Matter 16:

The same operation as for the Carrier for Adsorbing Organic Matter 1 was carried out, and the fiber diameter of the sea-island type solid composite fibers contained in the Carrier for Adsorbing Organic Matter 16 was measured. The results are shown in Table 1.

Pore Volume Measurement of Sea-Island Type Solid Composite Fibers Contained in Carrier for Adsorbing Organic Matter 16:

The same operation as for the Carrier for Adsorbing Organic Matter 1 was carried out, and the pore volume of the sea-island type solid composite fibers contained in the Carrier for Adsorbing Organic Matter 16 was measured. The results are shown in Table 1.

Basic Functional Group Content Measurement of Sea-Island Type Solid Composite Fibers Contained in Carrier for Adsorbing Organic Matter 16:

The same operation as for the Carrier for Adsorbing Organic Matter 1 was carried out, and the basic functional group content of the sea-island type solid composite fibers contained in the Carrier for Adsorbing Organic Matter 16 was measured. The results are shown in Table 1.

Measurement of Distance from Surface of Sea-Island Type Solid Composite Fiber to Outermost Island Component in Sea-Island Type Solid Composite Fibers Contained in Carrier for Adsorbing Organic Matter 16:

The same operation as for the Carrier for Adsorbing Organic Matter 1 was carried out, and the distance from the surface of a sea-island type solid composite fiber to the outermost island component in the sea-island type solid composite fibers contained in the Carrier for Adsorbing Organic Matter 16 was measured. The results are shown in Table 1.

Measurement of Maximum Island Diameter of Island Components of Sea-Island Type Solid Composite Fibers Contained in Carrier for Adsorbing Organic Matter 16:

The same operation as for the Carrier for Adsorbing Organic Matter 1 was carried out, and the maximum island diameter of the island components in sea-island type solid composite fibers contained in the Carrier for Adsorbing Organic Matter 16 was measured. The results are shown in Table 1.

(Preparation of Carrier for Adsorbing Organic Matter 17)

The same operation as for Carrier for Adsorbing Organic Matter 1 was carried out except that Knitted Fabric G was used instead of Knitted Fabric A and that the amount of TEPA was changed from 0.24 g to 0.18 g, to obtain Knitted Fabric 17 which was a carrier for adsorbing organic matter (hereinafter, Carrier for Adsorbing Organic Matter 17).

Fiber Diameter Measurement of Sea-Island Type Solid Composite Fibers Contained in Carrier for Adsorbing Organic Matter 17:

The same operation as for the Carrier for Adsorbing Organic Matter 1 was carried out, and the fiber diameter of the sea-island type solid composite fibers contained in the Carrier for Adsorbing Organic Matter 17 was measured. The results are shown in Table 1.

Pore Volume Measurement of Sea-Island Type Solid Composite Fibers Contained in Carrier for Adsorbing Organic Matter 17:

The same operation as for the Carrier for Adsorbing Organic Matter 1 was carried out, and the pore volume of the sea-island type solid composite fibers contained in the Carrier for Adsorbing Organic Matter 17 was measured. The results are shown in Table 1.

Basic Functional Group Content Measurement of Sea-Island Type Solid Composite Fibers Contained in Carrier for Adsorbing Organic Matter 17:

The same operation as for the Carrier for Adsorbing Organic Matter 1 was carried out, and the basic functional group content of the sea-island type solid composite fibers contained in the Carrier for Adsorbing Organic Matter 17 was measured. The results are shown in Table 1.

Measurement of Distance from Surface of Sea-Island Type Solid Composite Fiber to Outermost Island Component in Sea-Island Type Solid Composite Fibers Contained in Carrier for Adsorbing Organic Matter 17:

The same operation as for the Carrier for Adsorbing Organic Matter 1 was carried out, and the distance from the surface of a sea-island type solid composite fiber to the outermost island component in the sea-island type solid composite fibers contained in the Carrier for Adsorbing Organic Matter 17 was measured. The results are shown in Table 1.

Measurement of Maximum Island Diameter of Island Components of Sea-Island Type Solid Composite Fibers Contained in Carrier for Adsorbing Organic Matter 17:

The same operation as for the Carrier for Adsorbing Organic Matter 1 was carried out, and the maximum island diameter of the island components in sea-island type solid composite fibers contained in the Carrier for Adsorbing Organic Matter 17 was measured. The results are shown in Table 1.

(Preparation of Carrier for Adsorbing Organic Matter 18)

The same operation as for Carrier for Adsorbing Organic Matter 1 was carried out except that Knitted Fabric G was used instead of Knitted Fabric A and that the amount of TEPA was changed from 0.24 g to 1.0 g, to obtain Knitted Fabric 18 which was a carrier for adsorbing organic matter (hereinafter, Carrier for Adsorbing Organic Matter 18).

Fiber Diameter Measurement of Sea-Island Type Solid Composite Fibers Contained in Carrier for Adsorbing Organic Matter 18:

The same operation as for the Carrier for Adsorbing Organic Matter 1 was carried out, and the fiber diameter of the sea-island type solid composite fibers contained in the Carrier for Adsorbing Organic Matter 18 was measured. The results are shown in Table 1.

Pore Volume Measurement of Sea-Island Type Solid Composite Fibers Contained in Carrier for Adsorbing Organic Matter 18:

The same operation as for the Carrier for Adsorbing Organic Matter 1 was carried out, and the pore volume of the sea-island type solid composite fibers contained in the Carrier for Adsorbing Organic Matter 18 was measured. The results are shown in Table 1.

Basic Functional Group Content Measurement of Sea-Island Type Solid Composite Fibers Contained in Carrier for Adsorbing Organic Matter 18:

The same operation as for the Carrier for Adsorbing Organic Matter 1 was carried out, and the basic functional group content of the sea-island type solid composite fibers contained in the Carrier for Adsorbing Organic Matter 18 was measured. The results are shown in Table 1.

Measurement of Distance from Surface of Sea-Island Type Solid Composite Fiber to Outermost Island Component in Sea-Island Type Solid Composite Fibers Contained in Carrier for Adsorbing Organic Matter 18:

The same operation as for the Carrier for Adsorbing Organic Matter 1 was carried out, and the distance from the surface of a sea-island type solid composite fiber to the outermost island component in the sea-island type solid composite fibers contained in the Carrier for Adsorbing Organic Matter 18 was measured. The results are shown in Table 1.

Measurement of Maximum Island Diameter of Island Components of Sea-Island Type Solid Composite Fibers Contained in Carrier for Adsorbing Organic Matter 18:

The same operation as for the Carrier for Adsorbing Organic Matter 1 was carried out, and the maximum island diameter of the island components in sea-island type solid composite fibers contained in the Carrier for Adsorbing Organic Matter 18 was measured. The results are shown in Table 1.

(Preparation of Carrier for Adsorbing Organic Matter 19)

The same operation as for Carrier for Adsorbing Organic Matter 1 was carried out except that Knitted Fabric G was used instead of Knitted Fabric A and that the amount of TEPA was changed from 0.24 g to 1.25 g, to obtain Knitted Fabric 19 which was a carrier for adsorbing organic matter (hereinafter, Carrier for Adsorbing Organic Matter 19).

Fiber Diameter Measurement of Sea-Island Type Solid Composite Fibers Contained in Carrier for Adsorbing Organic Matter 19:

The same operation as for the Carrier for Adsorbing Organic Matter 1 was carried out, and the fiber diameter of the sea-island type solid composite fibers contained in the Carrier for Adsorbing Organic Matter 19 was measured. The results are shown in Table 1.

Pore Volume Measurement of Sea-Island Type Solid Composite Fibers Contained in Carrier for Adsorbing Organic Matter 19:

The same operation as for the Carrier for Adsorbing Organic Matter 1 was carried out, and the pore volume of the sea-island type solid composite fibers contained in the Carrier for Adsorbing Organic Matter 19 was measured. The results are shown in Table 1.

Basic Functional Group Content Measurement of Sea-Island Type Solid Composite Fibers Contained in Carrier for Adsorbing Organic Matter 19:

The same operation as for the Carrier for Adsorbing Organic Matter 1 was carried out, and the basic functional group content of the sea-island type solid composite fibers contained in the Carrier for Adsorbing Organic Matter 19 was measured. The results are shown in Table 1.

Measurement of Distance from Surface of Sea-Island Type Solid Composite Fiber to Outermost Island Component in Sea-Island Type Solid Composite Fibers Contained in Carrier for Adsorbing Organic Matter 19:

The same operation as for the Carrier for Adsorbing Organic Matter 1 was carried out, and the distance from the surface of a sea-island type solid composite fiber to the outermost island component in the sea-island type solid composite fibers contained in the Carrier for Adsorbing Organic Matter 19 was measured. The results are shown in Table 1.

Measurement of Maximum Island Diameter of Island Components of Sea-Island Type Solid Composite Fibers Contained in Carrier for Adsorbing Organic Matter 19:

The same operation as for the Carrier for Adsorbing Organic Matter 1 was carried out, and the maximum island diameter of the island components in sea-island type solid composite fibers contained in the Carrier for Adsorbing Organic Matter 19 was measured. The results are shown in Table 1.

(Preparation of Column for Adsorption 1)

Carrier for Adsorbing Organic Matter 7 was packed at a density of 0.08 g/cm$^3$ in a cylindrical column having solution inlet and outlet at the top and bottom with an internal volume of 145 cm$^3$ (height: 12.5 cm, diameter: 4.1 cm), to prepare Column for Adsorption 1.

(Preparation of Column for Adsorption 2)

Carrier for Adsorbing Organic Matter 7 was packed at a density of 0.17 g/cm$^3$ in a cylindrical column having a solution inlet and outlet at the top and bottom with an internal volume of 145 cm$^3$ (height: 12.5 cm, diameter: 4.1 cm), to prepare Column for Adsorption 2.

(Preparation of Column for Adsorption 3)

Carrier for Adsorbing Organic Matter 7 was packed at a density of 0.22 g/cm$^3$ in a cylindrical column having a solution inlet and outlet at the top and bottom with an internal volume of 145 cm$^3$ (height: 12.5 cm, diameter: 4.1 cm), to prepare Column for Adsorption 3.

(Preparation of Column for Adsorption 4)

Carrier for Adsorbing Organic Matter 7 was packed at a density of 0.37 g/cm$^3$ in a cylindrical column having a solution inlet and outlet at the top and bottom with an internal volume of 145 cm$^3$ (height: 12.5 cm, diameter: 4.1 cm), to prepare Column for Adsorption 4.

(Preparation of Column for Adsorption 5)

Carrier for Adsorbing Organic Matter 7 was packed at a density of 0.45 g/cm$^3$ in a cylindrical column having a solution inlet and outlet at the top and bottom with an internal volume of 145 cm$^3$ (height: 12.5 cm, diameter: 4.1 cm), to prepare Column for Adsorption 5.

Example 1

Measurement of Adsorption Rate of Acid Orange 7 of Carrier for Adsorbing Organic Matter 4:

First, 0.0875 g of acid orange 7 in powder form, 0.41 g of sodium acetate trihydrate, 0.96 mL of acetic acid, and 24 mL of ion-exchanged water were mixed, and the mixture was further diluted to 100 times with ion-exchanged water. Thus, an acid orange 7 buffer solution having a concentration in acid orange 7 of $1.0\times10^{-4}$ M was prepared. Then, 170 mL of a mixture of 1.14 mL of acetic acid and 200 mL of ion-exchanged water, and 30.6 mL of a mixture of 1.36 g of sodium acetate trihydrate and 100 mL of water were further mixed to prepare an acetic acid buffer solution. Standard solutions were prepared by diluting the acid orange 7 buffer solution with ion-exchanged water to 2, 4, 8 and 16 times, and using a UV-visible spectrophotometer, the standard solutions were measured for the absorbance with a measurement wavelength of 450 nm and a reference wavelength of 600 nm. A calibration curve was prepared from the obtained absorbances and the acid orange 7 concentrations of the standard solutions. Carrier for Adsorbing Organic Matter 4 was cut out in a disk having a diameter of 6 mm and this disk was impregnated with 1.5 mL of the acetic acid buffer solution, and mixed by inversion for 20 minutes. After mixing, the Carrier for Adsorbing Organic Matter 4 was filtrated through a filter paper, and the adhering acetic acid buffer solution was removed by centrifugation at 150 rpm for 15 minutes. The Carrier for Adsorbing Organic Matter 4 after the centrifugation was added to a polypropylene container to which 1.0 mL of the acid orange 7 buffer solution had been added, and mixed by inversion for 2 hours. After mixing, only the Carrier for Adsorbing Organic Matter 4 was taken out with tweezers. The absorbance of the acid orange 7 buffer solution was similarly measured before and after the addition and mixture by inversion of the Carrier for Adsorbing Organic Matter 4, and the concentration of acid orange 7 was calculated using the calibration curve. The adsorption rate of the acid orange 7 per disk of Carrier for Adsorbing Organic Matter 4 was calculated using the following Equation 3. The results are shown in Table 2.

Adsorption Rate of Acid Orange 7 of Carrier for Adsorbing Organic Matter 4(%)={Acid Orange 7 Concentration in Acid Orange 7 Buffer Solution Before Addition of Carrier for Adsorbing Organic Matter 4 (M)–Acid Orange 7 Concentration in Acid Orange 7 Buffer Solution After Addition of Carrier for Adsorbing Organic Matter 4 (M)}/Acid Orange 7 Concentration in Acid Orange 7 Buffer Solution Before Addition of Carrier for Adsorbing Organic Matter 4 (M)×100  Equation 3

Measurement of Adsorption Rate of IL-8 of Carrier for Adsorbing Organic Matter 4:

In order to confirm the adsorption ability of IL-8 of Carrier for Adsorbing Organic Matter 4, the Carrier for Adsorbing Organic Matter 4 was impregnated with a liquid containing IL-8 for a predetermined time and taken out, and then the adsorption rate of IL-8 was measured from the difference in the IL-8 amount in the liquid before and after the impregnation. The measurement method will be described below.

Carrier for Adsorbing Organic Matter 4 was cut into disks having a diameter of 6 mm, four of which were put into a polypropylene container. To the container, a FBS solution that was prepared such that the concentration of IL-8 would be 2000 pg/mL was added in an amount of 30 mL per 1 cm$^3$ of Carrier for Adsorbing Organic Matter 4. The resulting mixture was mixed by inversion for 2 hours in an incubator at 37° C., and then the concentration of IL-8 in the FBS solution was measured by ELISA. The adsorption rate of IL-8 was calculated from the IL-8 concentration measured before and after the mixture by inversion, using the following Equation 4. The results are shown in Table 2.

Adsorption Rate of IL-8 of Carrier for Adsorbing Organic Matter 4(%)={Concentration of IL-8 Before Mixture by Inversion (pg/mL)–Concentration of IL-8 After Mixture by Inversion (pg/mL)}/Concentration of IL-8 Before Mixture by Inversion (pg/mL)×100  Equation 4

Measurement of Adsorption Rate of IL-6 of Carrier for Adsorbing Organic Matter 4:

In order to confirm the adsorption ability of IL-6 of Carrier for Adsorbing Organic Matter 4, the Carrier for Adsorbing Organic Matter 4 was impregnated with a liquid containing IL-6 for a predetermined time and taken out, and then the adsorption rate of IL-6 was measured from the difference in the IL-6 amount in the liquid before and after the impregnation. The measurement method will be described below.

Carrier for Adsorbing Organic Matter 4 was cut into disks having a diameter of 6 mm, four of which were put into a polypropylene container. To the container, a FBS solution that was prepared such that the concentration of IL-6 would be 2000 pg/mL was added in an amount of 30 mL per 1 cm$^3$ of Carrier for Adsorbing Organic Matter 4. The resulting mixture was mixed by inversion for 2 hours in an incubator at 37° C., and then the concentration of IL-6 in the FBS solution was measured by ELISA. The adsorption rate of IL-6 was calculated from the IL-6 concentration measured before and after the mixture by inversion, using the following Equation 5. The results are shown in Table 2.

Adsorption Rate of IL-6 of Carrier for Adsorbing Organic Matter 4(%)={Concentration of IL-6 Before Mixture by Inversion (pg/mL)−Concentration of IL-6 After Mixture by Inversion (pg/mL)}/Concentration of IL-6 Before Mixture by Inversion (pg/mL)×100      Equation 5

Measurement of Adsorption Rate of HMGB-1 of Carrier for Adsorbing Organic Matter 4:

In order to confirm the adsorption ability of HMGB-1 of Carrier for Adsorbing Organic Matter 4, the Carrier for Adsorbing Organic Matter 4 was impregnated with a liquid containing HMGB-1 for a predetermined time and taken out, and then the adsorption rate of HMGB-1 was measured from the difference in the HMGB-1 amount in the liquid before and after the impregnation. The measurement method will be described below.

Carrier for Adsorbing Organic Matter 4 was cut into disks having a diameter of 6 mm, four of which were put into a polypropylene container. To the container, a FBS solution that was prepared such that the concentration of HMGB-1 would be 100 ng/mL was added in an amount of 30 mL per 1 cm$^3$ of Carrier for Adsorbing Organic Matter 4. The resulting mixture was mixed by inversion for 2 hours in an incubator at 37° C., and then the concentration of HMGB-1 in the FBS solution was measured by ELISA. The adsorption rate of HMGB-1 was calculated from the HMGB-1 concentration measured before and after the mixture by inversion, using the following Equation 6. The results are shown in Table 2.

Adsorption Rate of HMGB-1 of Carrier for Adsorbing Organic Matter 4(%)={Concentration of HMGB-1 Before Mixture by Inversion (ng/mL)−Concentration of HMGB-1 After Mixture by Inversion (ng/mL)}/Concentration of HMGB-1 Before Mixture by Inversion (ng/mL)×100      Equation 6

Measurement of Possible Duration of Liquid Passage Through Column of Carrier for Adsorbing Organic Matter 4:

A healthy rabbit was used to measure the possible duration of liquid passage through the column of Carrier for Adsorbing Organic Matter 4. First, after anesthesia induction through intravenous administration of 30 mg/kg of pentobarbital sodium (25 mg/mL, NACALAI TESQUE, INC.), a NZW male rabbit (body weight: 3 to 3.5 kg) was shaved at the neck and abdomen. After subcutaneous injection of lidocaine (Xylocaine Injection 0.5%, AstraZeneca K.K.), the trachea was exposed from the neck. A tracheal cannula (16 Fr, Terumo Corporation) was intubated and immobilized to the trachea. A respirator (EVITA 300, Draeger Medical Japan LTD.) was used to perform ventilation. Conditions of the ventilation were regulated by measuring parameters of blood gas of blood collected from a carotid artery with positive end-expiratory pressure (PEEP) applied through i-STAT (cartridge CG4+, ABBOTT JAPAN CO., LTD.) and changing the number of ventilation such that the measurements (values corrected to a body temperature) were within the pCO$_2$ range of 35 to 45 mmHg. An inspired oxygen concentration was set to 100%, and after the conditions of the ventilation was set, evaluation of the equipment to be tested was started. During the evaluation, the conditions of the ventilation were not changed. An infusion of 0.06 mg/kg/hr of vecuronium dissolved in normal saline (VECURONIUM 4 mg for intravenous injection: Fuji Pharma, Co., Ltd., normal saline: Otsuka Pharmaceutical Factory, Inc.) was given by continuous infusion of 2 mL/kg/hr. The infusion was further connected to an infusion pump (55-1111, HARVARD APPARATUS, INC.) via a three way stopcock to achieve a route of maintenance anesthesia. As maintenance anesthesia, pentobarbital (12.5 mg/mL, NACALAI TESQUE INC.) was given by continuous infusion of 2 to 8 mg/kg/hr (decreased or increased in accordance with state of the animal). Carrier for Adsorbing Organic Matter 4 was packed at a density of 0.35 g/cm$^3$ in a cylindrical mini column with a packing volume of 11 cm$^3$ (packing height: 4.7 cm, packing diameter: 1.9 cm), to prepare a column for rabbit extracorporeal circulation. This column was washed with normal saline, and after priming a heparin, was executed at a flow rate of 5 mL/min to the healthy rabbit. For the evaluation of the pressure increase, using the difference between the pressure applied to the inlet side and the pressure applied to the outlet side of the column for rabbit extracorporeal circulation (hereinafter, differential pressure) as an index, the time from the start of circulation to the moment where the differential pressure exceeded 100 mmHg (60 minutes at maximum) was measured as the possible duration of liquid passage through the column. The results are shown in Table 2.

Measurement of Amount of Generated Fine Particles of Carrier for Adsorbing Organic Matter 4:

Carrier for Adsorbing Organic Matter 4 was cut into a disk having a diameter of 26 mm, and placed in a clean container together with 50 mL of ion-exchanged water (filtrated water) that had passed through an HEPA filter with a pore size of 0.3 μm. The resulting mixture was mixed by 10 inversions, and then washed after the liquid was discharged. This washing operation was repeated once more. The washed knitted fabric to be tested was placed on the base plate attached to a stirring-type ultraholder UHP-25K (manufactured by ADVANTEC Co., Ltd.), and after the O-ring was placed thereon, the washed knitted fabric was sandwiched with the cylindrical container (cell) having a diameter of 18 mm and fixed with the base mounting bracket. The liquid outlet of the base plate was closed with a silicone tube, and 10 mL of filtrated water was added with the knitted fabric on the bottom side, and it was confirmed that there was no water leakage. A stirring set attached to UHP-25K was installed, and stirring was performed on a magnetic stirrer RCN-7 (manufactured by Tokyo Rika Kikai Co., Ltd.) at a rotation speed of 600 rpm for 5 minutes in a way that the stirring set was not in contact with the knitted fabric. This liquid was collected, and 3 mL of the liquid was measured with a light obscuration automatic particle counter KL-04 (manufactured by Rion Co., Ltd.), and the amount of fine particles of not less than 10 μm per 1 mL was measured as the amount of generated fine particles (unit: particles/mL). The results are shown in Table 2.

Example 2

The same measurements as in Example 1 were performed except that Carrier for Adsorbing Organic Matter 5 was used instead, and the adsorption rate of acid orange 7, the adsorption rate of IL-8, the adsorption rate of IL-6, the adsorption rate of HMGB-1, the possible duration of liquid passage through the column, and the amount of generated fine particles were measured. The results are shown in Table 2.

Example 3

The same measurements as in Example 1 were performed except that Carrier for Adsorbing Organic Matter 7 was used instead, and the adsorption rate of acid orange 7, the adsorption rate of IL-8, the adsorption rate of IL-6, the adsorption rate of HMGB-1, the possible duration of liquid passage through the column, and the amount of generated fine particles were measured. The results are shown in Table 2.

Example 4

The same measurements as in Example 1 were performed except that Carrier for Adsorbing Organic Matter 8 was used instead, and the adsorption rate of acid orange 7, the adsorption rate of IL-8 the adsorption rate of IL-6, the adsorption rate of HMGB-1, the possible duration of liquid passage through the column, and the amount of generated fine particles were measured. The results are shown in Table 2.

Example 5

The same measurements as in Example 1 were performed except that Carrier for Adsorbing Organic Matter 9 was used instead, and the adsorption rate of acid orange 7, the adsorption rate of IL-8, the adsorption rate of IL-6, the adsorption rate of HMGB-1, the possible duration of liquid passage through the column, and the amount of generated fine particles were measured. The results are shown in Table 2.

Example 6

The same measurements as in Example 1 were performed except that Carrier for Adsorbing Organic Matter 11 was used instead, and the adsorption rate of acid orange 7, the adsorption rate of IL-8, the adsorption rate of IL-6, the adsorption rate of HMGB-1, the possible duration of liquid passage through the column, and the amount of generated fine particles were measured. The results are shown in Table 2.

Example 7

The same measurements as in Example 1 were performed except that Carrier for Adsorbing Organic Matter 13 was used instead, and the adsorption rate of acid orange 7, the adsorption rate of IL-8, and the amount of generated fine particles were measured. The results are shown in Table 3.

Example 8

The same measurements as in Example 1 were performed except that Carrier for Adsorbing Organic Matter 14 was used instead, and the adsorption rate of acid orange 7, the adsorption rate of IL-8, and the amount of generated fine particles were measured. The results are shown in Table 3.

Example 9

The same measurements as in Example 1 were performed except that Carrier for Adsorbing Organic Matter 15 was used instead, and the adsorption rate of acid orange 7, the adsorption rate of IL-8, and the amount of generated fine particles were measured. The results are shown in Table 3.

Example 10

The same measurements as in Example 1 were performed except that Carrier for Adsorbing Organic Matter 16 was used instead, and the adsorption rate of acid orange 7, the adsorption rate of IL-8, and the amount of generated fine particles were measured. The results are shown in Table 3.

Example 11

The same measurements as in Example 1 were performed except that Carrier for Adsorbing Organic Matter 17 was used instead, and the adsorption rate of acid orange 7, the adsorption rate of IL-8, and the amount of generated fine particles were measured. The results are shown in Table 3.

Example 12

The same measurements as in Example 1 were performed except that Carrier for Adsorbing Organic Matter 18 was used instead, and the adsorption rate of acid orange 7, the adsorption rate of IL-8, and the amount of generated fine particles were measured. The results are shown in Table 3.

Example 13

The same measurements as in Example 1 were performed except that Carrier for Adsorbing Organic Matter 19 was used instead, and the adsorption rate of acid orange 7, the adsorption rate of IL-8, and the amount of generated fine particles were measured. The results are shown in Table 3.

Example 14

Pressure Loss Measurement Test of Column for Adsorption 1:

The Column for Adsorption 1 was connected as shown in FIG. 3, and the FBS solution was kept warm at 37° C. (outside temperature). Then, 2500 mL of the FBS solution to which IL-8 was added such that the concentration thereof would be 2000 pg/mL was pooled in a constant temperature water bath. The foregoing FBS solution was passed through the Column for Adsorption 1 at a flow rate of 100 mL/min for 2 hours, and the pressure during the liquid passage was measured by the inlet pressure measurement device 9 and the outlet pressure measurement device 10. The value obtained by subtracting the pressure measured by the outlet pressure measurement device from the pressure measured by the inlet pressure measurement device was determined as the pressure loss. Furthermore, after the liquid passage though the Column for Adsorption 1 for 2 hours, the IL-8 concentration in the FBS solution was measured by ELISA. From the reduction rate from 2000 pg/mL, the IL-8 circulation adsorption rate was obtained. The results of pressure loss and IL-8 circulation adsorption rate are shown in Table 4.

Example 15

The same measurements as in Example 14 were performed except that Column for Adsorption 2 was used instead, to obtain the pressure loss and the IL-8 circulation adsorption rate. The results are shown in Table 4.

Example 16

The same measurements as in Example 14 were performed except that Column for Adsorption 3 was used instead, to obtain the pressure loss and the IL-8 circulation adsorption rate. The results are shown in Table 4.

Example 17

The same measurements as in Example 14 were performed except that Column for Adsorption 4 was used instead, to obtain the pressure loss and the IL-8 circulation adsorption rate. The results are shown in Table 4.

Example 18

The same measurements as in Example 14 were performed except that Column for Adsorption 5 was used instead, to measure the pressure loss and IL-8 circulation adsorption rate. The results are shown in Table 4.

Example 19

Measurement of Circularity of Carriers for Adsorbing Organic Matter 4, 5, 7 to 9, 11, 13 to 19:

In an Image of a cross section of a sample of the sea-island type solid composite fibers contained in Carrier for Adsorbing Organic Matter 4, which was cut perpendicular to the fiber axis direction, 10 positions were randomly selected and photographed at a magnification at which the island components could be clearly observed by SEM. A minimum enclosing circle (2 in FIG. 1) was created on the obtained images of the fiber cross sections, and the radius was calculated in units of 0.1 µm. Further, a maximum circle that was concentric with the minimum enclosing circle and could be included inside the fiber (hereinafter, maximum inscribed circle, 3 in FIG. 1) was created on the fiber cross sections, and the radius was calculated in units of 0.1 µm. The circularity was the value obtained by subtracting the radius of the maximum inscribed circle from the radius of the minimum enclosing circle. Further, the circularity of each of the Carriers for Adsorbing Organic Matter 5, 7 to 9, 11, and 13 to 19 was also measured in the same manner as for Carrier for Adsorbing Organic Matter 4. As a result, the circularity of each of Carriers for Adsorbing Organic Matter 4, 5, 7 to 9, 11, 13 to 19 was in the range of 0 to 15 µm.

Comparative Example 1

The same measurements as in Example 1 were performed except that Carrier for Adsorbing Organic Matter 1 was used instead, and the adsorption rate of acid orange 7, the adsorption rate of IL-8, the adsorption rate of IL-6, the adsorption rate of HMGB-1, the possible duration of liquid passage through the column, and the amount of generated fine particles were measured. The results are shown in Table 2.

Comparative Example 2

The same measurements as in Example 1 were performed except that Carrier for Adsorbing Organic Matter 2 was used instead, and the adsorption rate of acid orange 7, the adsorption rate of IL-8, the adsorption rate of IL-6, the adsorption rate of HMGB-1, the possible duration of liquid passage through the column, and the amount of generated fine particles were measured. The results are shown in Table 2.

Comparative Example 3

The same measurements as in Example 1 were performed except that Carrier for Adsorbing Organic Matter 3 was used instead, and the adsorption rate of acid orange 7, the adsorption rate of IL-8, the adsorption rate of IL-6, the adsorption rate of HMGB-1, the possible duration of liquid passage through the column, and the amount of generated fine particles were measured. The results are shown in Table 2.

Comparative Example 4

The same measurements as in Example 1 were performed except that Carrier for Adsorbing Organic Matter 6 was used instead, and the adsorption rate of acid orange 7, the adsorption rate of IL-8, the adsorption rate of IL-6, the adsorption rate of HMGB-1, the possible duration of liquid passage through the column, and the amount of generated fine particles were measured. The results are shown in Table 2.

Comparative Example 5

The same measurements as in Example 1 were performed except that Carrier for Adsorbing Organic Matter 10 was used instead, and the adsorption rate of acid orange 7, the adsorption rate of IL-8, the adsorption rate of IL-6, the adsorption rate of HMGB-1, the possible duration of liquid passage through the column, and the amount of generated fine particles were measured. The results are shown in Table 2.

Comparative Example 6

The same measurements as in Example 1 were performed except that Carrier for Adsorbing Organic Matter 12 was used instead, and the adsorption rate of acid orange 7, the adsorption rate of IL-8, the adsorption rate of IL-6, the adsorption rate of HMGB-1, the possible duration of liquid passage through the column, and the amount of generated fine particles were measured. The results are shown in Table 2.

Comparative Example 7

Measurement of Circularity of Carriers for Adsorbing Organic Matter 1 to 3, 6, 10, and 12:

The circularity of each of Carriers for Adsorbing Organic Matter 1 to 3, 6, 10, and 12 was measured in the same manner as for Carrier for Adsorbing Organic Matter 4. The circularity of Carrier for Adsorbing Organic Matter 12 was 18 µm, and the circularities of Carriers for Adsorbing Organic Matter 1 to 3, 6 and 10 were all in the range of 0 to 15 µm.

TABLE 1

| Name of Carrier for Adsorption | Fiber Diameter μm | Pore Volume cm³/g | Distance from Sea-island Type Solid Composite Fiber Surface to Outermost Island Component μm | Maximum Island Diameter μm | Basic Functional Group Content mmol/g |
|---|---|---|---|---|---|
| Carrier for Adsorption 1 | 5 | 0.03 | 1.2 | 3.0 | 1.1 |
| Carrier for Adsorption 2 | 5 | 0.27 | 1.6 | 3.0 | 1.5 |
| Carrier for Adsorption 3 | 20 | 0.07 | 1.3 | 4.4 | 1.1 |
| Carrier for Adsorption 4 | 25 | 0.12 | 2.2 | 0.6 | 1.3 |
| Carrier for Adsorption 5 | 30 | 0.07 | 1.7 | 0.7 | 1.2 |
| Carrier for Adsorption 6 | 35 | 0.03 | 2.0 | 1.0 | 1.1 |
| Carrier for Adsorption 7 | 35 | 0.21 | 3.8 | 0.8 | 1.3 |
| Carrier for Adsorption 8 | 35 | 0.21 | 3.1 | 0.8 | 0 |
| Carrier for Adsorption 9 | 35 | 0.48 | 3.0 | 0.8 | 1.1 |
| Carrier for Adsorption 10 | 35 | 0.59 | 10.5 | 1.2 | 1.4 |
| Carrier for Adsorption 11 | 55 | 0.35 | 5.1 | 1.1 | 1.3 |
| Carrier for Adsorption 12 | 65 | 0.22 | 4.7 | 1.4 | 1.3 |
| Carrier for Adsorption 13 | 35 | 0.20 | 3.5 | 1.4 | 1.0 |
| Carrier for Adsorption 14 | 35 | 0.21 | 3.6 | 1.6 | 1.2 |
| Carrier for Adsorption 15 | 35 | 0.23 | 3.7 | 2.5 | 1.1 |
| Carrier for Adsorption 16 | 33 | 0.16 | 3.3 | 0.8 | 0.4 |
| Carrier for Adsorption 17 | 34 | 0.18 | 3.2 | 0.8 | 0.7 |
| Carrier for Adsorption 18 | 36 | 0.25 | 3.5 | 0.8 | 4.8 |
| Carrier for Adsorption 19 | 36 | 0.28 | 3.6 | 0.8 | 5.2 |

In Table 1, "Name of Carrier for Adsorption" indicates the name of the carrier for adsorbing organic matter, "Fiber Diameter" indicates the fiber diameter of the sea-island type solid composite fibers contained in the carrier for adsorbing organic matter, and "Pore Volume" indicates the pore volume of the sea-island type solid composite fibers contained in the carrier for adsorbing organic matter, "Distance from Sea-island Type Solid Composite Fiber Surface to Outermost Island Component" indicates the distance from the surface of the sea-island type solid composite fiber to the outermost island component in a cross section perpendicular to the fiber axis direction of the sea-island type solid composite fibers contained in the carrier for adsorbing organic matter, "Maximum Island Diameter" indicates the maximum island diameter of the island components of the sea-island type solid composite fibers contained in the carrier for adsorbing organic matter, and "Basic Functional Group Content" indicates the basic functional group content per 1 g of dry weight of the sea-island type solid composite fibers contained in the carrier for adsorbing organic matter.

TABLE 2

| | | | PGP-23 | | | | |
|---|---|---|---|---|---|---|---|
| | Name of Carrier for Adsorption | Acid Orange 7 Adsorption Rate % | IL-8 Adsorption Rate % | IL-6 Adsorption Rate % | HMGB-1 Adsorption Rate % | Possible Duration of Liquid Passage Through Column min | Amount of Generated Fine Particles Particles/mL |
| Example 1 | Carrier for Adsorption 4 | 52 | 58 | 71 | 75 | 60 | 5 |
| Example 2 | Carrier for Adsorption 5 | 48 | 51 | 66 | 70 | >60 | 5 |
| Example 3 | Carrier for Adsorption 7 | 59 | 71 | 75 | 81 | >60 | 10 |
| Example 4 | Carrier for Adsorption 8 | 45 | 4 | 1 | 9 | >60 | 8 |

TABLE 2-continued

| | | | PGP-23 | | | | |
|---|---|---|---|---|---|---|---|
| | Name of Carrier for Adsorption | Acid Orange 7 Adsorption Rate % | IL-8 Adsorption Rate % | IL-6 Adsorption Rate % | HMGB-1 Adsorption Rate % | Possible Duration of Liquid Passage Through Column min | Amount of Generated Fine Particles Particles/mL |
| Example 5 | Carrier for Adsorption 9 | 56 | 60 | 73 | 80 | >60 | 11 |
| Example 6 | Carrier for Adsorption 11 | 46 | 67 | 62 | 70 | >60 | 7 |
| Comparative Example 1 | Carrier for Adsorption 1 | 51 | 51 | 58 | 62 | 12 | 5 |
| Comparative Example 2 | Carrier for Adsorption 2 | 53 | 66 | 65 | 73 | 10 | 7 |
| Comparative Example 3 | Carrier for Adsorption 3 | 50 | 61 | 63 | 65 | 51 | 4 |
| Comparative Example 4 | Carrier for Adsorption 6 | 2 | 5 | 3 | 15 | >60 | 1 |
| Comparative Example 5 | Carrier for Adsorption 10 | 32 | 33 | 40 | 50 | >60 | 28 |
| Comparative Example 6 | Carrier for Adsorption 12 | 15 | 21 | 26 | 33 | >60 | 8 |

In Table 2, "Name of Carrier for Adsorption" indicates the name of the carrier for adsorbing organic matter, and those having >60 for Possible Duration of Liquid Passage Through Column indicate that a differential pressure upon the circulation for 60 minutes is less than 50 mmHg, suggesting a high standard because the circulation for 120 minutes or longer in total is highly possible. Further, those having 60 for Possible Duration of Liquid Passage Through Column indicate that a differential pressure upon the circulation for 60 minutes is not less than 50 mmHg, suggesting a concern that the circulation is interrupted within 120 minutes in total.

The results of Table 2 have shown that the carriers for adsorbing organic matter of the present embodiments can ensure a liquid passage duration of 60 minutes by suppressing a pressure increase when packed in a column, and are excellent in adsorbing organic matter, particularly blood components. It has also been shown that the amount of generated fine particles is appropriately suppressed. In Example 1, the liquid could be passed through the column for 60 minutes, but the differential pressure exceeded 50 mmHg. Therefore, it is believed that there is a risk if the circulation is further continued.

In Table 3. "Name of Carrier for Adsorption" indicates the name of the carrier for adsorbing organic matter.

The results of Table 3 have shown that the carriers for adsorbing organic matter of the present embodiments are excellent in adsorbing organic matter, particularly blood components. It has also been shown that, when the basic functional group content is in the range of 0.5 to 5.0 mmol per 1 g of dry weight of the sea-island type solid composite fibers, the amount of the adsorption of organic matter, especially blood components is excellent, and the amount of generated fine particles is appropriately suppressed. Furthermore, it has been found that, when the maximum island diameter of the island components of the sea-island type solid composite fibers is in the range of 0.1 to 2 μm, the amount of the adsorption of organic matter, especially blood components is excellent, and the amount of generated fine particles is appropriately suppressed.

TABLE 3

| | Name of Carrier for Adsorption | Acid Orange 7 Adsorption Rate % | IL-8 Adsorption Rate % | Amount of Generated Fine Particles Particles/mL |
|---|---|---|---|---|
| Example 7 | Carrier for Adsorption 13 | 55 | 65 | 8 |
| Example 8 | Carrier for Adsorption 14 | 57 | 72 | 21 |
| Example 9 | Carrier for Adsorption 15 | 54 | 60 | 32 |
| Example 10 | Carrier for Adsorption 16 | 48 | 25 | 2 |
| Example 11 | Carrier for Adsorption 17 | 52 | 70 | 8 |
| Example 12 | Carrier for Adsorption 18 | 71 | 51 | 15 |
| Example 13 | Carrier for Adsorption 19 | 74 | 18 | 20 |

TABLE 4

|  | Name of Column for Adsorption | Packing Density g/cm³ | IL-8 Circulation Adsorption Rate % | Pressure Loss mmHg |
|---|---|---|---|---|
| Example 14 | Column for Adsorption 1 | 0.08 | 21 | 5 |
| Example 15 | Column for Adsorption 2 | 0.17 | 44 | 15 |
| Example 16 | Column for Adsorption 3 | 0.22 | 58 | 25 |
| Example 17 | Column for Adsorption 4 | 0.37 | 68 | 70 |
| Example 18 | Column for Adsorption 5 | 0.45 | 70 | 150 |

The results of Table 4 have shown that the columns for adsorption comprising a carrier for adsorbing organic matter of the present embodiments are, when the packing density of the carrier for adsorbing organic matter is in the range of 0.15 to 0.40 g/cm³, excellent especially in the circulation adsorption rate of blood components while suppressing the pressure loss during the circulation.

INDUSTRIAL APPLICABILITY

The carrier for adsorbing organic matter of the present embodiments and the column comprising the carrier for adsorbing organic matter can be used for treatment of biological components, particularly for treatment of blood components, in the medical field.

REFERENCE SIGNS LIST

1: Sea-island Type Solid Composite Fiber
2: Minimum Enclosing Circle
3: Maximum Inscribed Circle
4: Sea Component
5: Island Component
d1: Shortest Distance from Fiber Surface to Outermost Island Component in One of 6-divided Cross Sections
d2: Shortest Distance from Fiber Surface to Outermost Island Component in One of 6-divided Cross Sections
d3: Shortest Distance from Fiber Surface to Outermost Island Component in One of 6-divided Cross Sections
d4: Shortest Distance from Fiber Surface to Outermost Island Component in One of 6-divided Cross Sections
d5: Shortest Distance from Fiber Surface to Outermost Island Component in One of 6-divided Cross Sections
d6: Shortest Distance from Fiber Surface to Outermost Island Component in One of 6-divided Cross Sections
6: FBS solution
7: Pump
8: Column for Adsorption
9: Inlet Pressure Measurement Device
10: Outlet Pressure Measurement Device
11: Constant Temperature Water Bath
12: Heater
13: Circuit

The invention claimed is:

1. A carrier for adsorbing organic matter, comprising a sea-island solid composite fiber which has a pore volume of 0.05 to 0.5 cm³/g and a fiber diameter of 25 to 60 μm.

2. The carrier for adsorbing organic matter, according to claim 1, comprising a ligand having an acidic functional group or a basic functional group on the surface of said sea-island solid composite fiber, wherein the content of said acidic functional group or said basic functional group is 0.5 to 5.0 mmol per 1 g dry weight of said sea-island solid composite fiber.

3. The carrier for adsorbing organic matter, according to claim 1, wherein the sea component of said sea-island solid composite fiber is composed of a single thermoplastic resin, and the island component of said sea-island solid composite fiber is composed of polyolefin.

4. The carrier for adsorbing organic matter, according to claim 1, wherein the distance from the surface of said sea-island solid composite fiber to the outermost island component in a cross section perpendicular to the fiber axis direction of said sea-island solid composite fiber is not less than 1 μm and less than 30 μm, and the maximum island diameter of the island component of said sea-island solid composite fiber is 0.1 to 2 μm.

5. The carrier for adsorbing organic matter, according to claim 1, which is for adsorbing and removing blood components.

6. A column for adsorption, comprising the carrier for adsorbing organic matter, according to claim 1.

7. A column for adsorption, comprising the carrier for adsorbing organic matter, according to claim 1, wherein the packing density of said carrier for adsorbing organic matter is 0.15 to 0.40 g/cm³.

8. A method for adsorbing organic matter, comprising:
contacting a liquid containing the organic matter with a carrier to adsorb the organic matter, said carrier comprising a sea-island solid composite fiber which has a pore volume of 0.05 to 0.5 cm³/g and a fiber diameter of 25 to 60 μm.

9. The method according to claim 8, wherein the carrier comprises a ligand having an acidic functional group or a basic functional group on the surface of said sea-island solid composite fiber, and wherein the content of said acidic functional group or said basic functional group is 0.5 to 5.0 mmol per 1 g dry weight of said sea-island solid composite fiber.

10. The method according to claim 8, wherein the sea component of said sea-island solid composite fiber is composed of a single thermoplastic resin, and the island component of said sea-island solid composite fiber is composed of polyolefin.

11. The method according to claim 8, wherein the distance from the surface of said sea-island solid composite fiber to the outermost island component in a cross section perpendicular to the fiber axis direction of said sea-island solid composite fiber is not less than 1 μm and less than 30 μm, and the maximum island diameter of the island component of said sea-island solid composite fiber is 0.1 to 2 μm.

12. The method according to claim 8, which is for adsorbing and removing blood components.

13. A method for adsorbing organic matter, comprising:
contacting a liquid containing the organic matter with a column to adsorb the organic matter, said column comprising a carrier comprising a sea-island solid composite fiber which has a pore volume of 0.05 to 0.5 cm$^3$/g and a fiber diameter of 25 to 60 µm.

14. The method according to claim 13, wherein the carrier comprises a ligand having an acidic functional group or a basic functional group on the surface of said sea-island solid composite fiber, and
wherein the content of said acidic functional group or said basic functional group is 0.5 to 5.0 mmol per 1 g dry weight of said sea-island solid composite fiber.

15. The method according to claim 13, wherein the sea component of said sea-island solid composite fiber is composed of a single thermoplastic resin, and
the island component of said sea-island solid composite fiber is composed of polyolefin.

16. The method according to claim 13, wherein the distance from the surface of said sea-island solid composite fiber to the outermost island component in a cross section perpendicular to the fiber axis direction of said sea-island solid composite fiber is not less than 1 µm and less than 30 µm, and the maximum island diameter of the island component of said sea-island solid composite fiber is 0.1 to 2 µm.

17. The method according to claim 13, which is for adsorbing and removing blood components.

\* \* \* \* \*